(12) United States Patent
States et al.

(10) Patent No.: US 10,221,249 B2
(45) Date of Patent: Mar. 5, 2019

(54) METHOD OF MAKING PATIENT SPECIFIC ANTI-IDIOTYPE ANTIBODIES

(71) Applicant: Affigen, LLC, St. Louis, MO (US)

(72) Inventors: David J. States, Ann Arbor, MI (US); Carlos F. Santos, University City, MO (US)

(73) Assignee: Affigen, LLC, St. Louis, MO (US)

( * ) Notice: Subject to any disclaimer, the term of this patent is extended or adjusted under 35 U.S.C. 154(b) by 0 days.

(21) Appl. No.: 15/261,084

(22) Filed: Sep. 9, 2016

(65) Prior Publication Data
US 2017/0073432 A1  Mar. 16, 2017

Related U.S. Application Data

(60) Provisional application No. 62/216,992, filed on Sep. 10, 2015.

(51) Int. Cl.
| | |
|---|---|
| C07K 16/42 | (2006.01) |
| C07K 16/28 | (2006.01) |
| C07K 16/30 | (2006.01) |
| A61K 39/00 | (2006.01) |

(52) U.S. Cl.
CPC .......... C07K 16/4241 (2013.01); C07K 16/28 (2013.01); C07K 16/30 (2013.01); *A61K 2039/505* (2013.01); *C07K 2317/14* (2013.01); *C07K 2317/24* (2013.01); *C07K 2317/31* (2013.01); *C07K 2317/55* (2013.01); *C07K 2317/622* (2013.01)

(58) Field of Classification Search
CPC .................................................. C07K 16/4241
See application file for complete search history.

(56) References Cited

U.S. PATENT DOCUMENTS

| | | | |
|---|---|---|---|
| 4,661,586 A | 4/1987 | Levy et al. | |
| 4,816,249 A | 3/1989 | Levy et al. | |
| 5,885,793 A * | 3/1999 | Griffiths | C07K 16/005 435/252.3 |
| 8,435,539 B2 | 5/2013 | McBride et al. | |
| 8,592,562 B2 | 11/2013 | Kannan et al. | |
| 8,652,484 B2 | 2/2014 | McBride et al. | |
| 8,969,318 B2 | 3/2015 | Toleikis et al. | |
| 9,725,768 B2 * | 8/2017 | Santos | C07K 16/00 |
| 2003/0138432 A1 | 7/2003 | Glazier | |
| 2007/0134249 A1 | 6/2007 | Denney et al. | |
| 2008/0317751 A1 | 12/2008 | Heath | |
| 2009/0324603 A1 | 12/2009 | Cao | |
| 2012/0141462 A1 | 6/2012 | Messmer et al. | |
| 2013/0022538 A1 | 1/2013 | Rossi et al. | |
| 2013/0337049 A1 | 12/2013 | Vater et al. | |
| 2015/0080266 A1 | 3/2015 | Volkmuth et al. | |

FOREIGN PATENT DOCUMENTS

| | | | |
|---|---|---|---|
| WO | WO-9615153 A1 | 5/1996 | |
| WO | WO-9626271 A1 | 8/1996 | |
| WO | WO-03008930 A2 | 1/2003 | |
| WO | WO-03059155 A2 | 7/2003 | |
| WO | WO-2012025530 A1 | 3/2012 | |
| WO | WO-2012138475 A1 | 10/2012 | |
| WO | WO-2014036488 A1 * | 3/2014 | ............. C07K 16/00 |
| WO | WO-2014056783 A1 | 4/2014 | |
| WO | WO-2014089152 A1 | 6/2014 | |
| WO | WO-2015013461 A2 | 1/2015 | |
| WO | WO-2015048462 A1 | 4/2015 | |

OTHER PUBLICATIONS

International Preliminary Report on Patentability for PCT/US2016/051120, published Mar. 16, 2017, 22 pages.
Altschul, et al. Basic local alignment search tool. J Mol Biol. Oct. 5, 1990;215(3):403-10.
Altschul, et al. Gapped BLAST and PSI-BLAST: a new generation of protein database search programs. Nucleic Acids Res. Sep. 1, 1997;25(17):3389-402.
Andreeff, et al. Discrimination of human leukemia subtypes by flow cytometric analysis of cellular DNA and RNA. Blood. Feb. 1980;55(2):282-93.
Ausubel, et al. Current Protocols in Molecular Biology. Dec. 4, 2003. Copyright 2003. John Wiley & Sons, Inc. ISBN: 047150338X. 4648 pages.
Basham, et al. Synergistic antitumor activity with IFN and monoclonal anti-idiotype for murine B cell lymphoma: Mechanism of action. J Immunol. Oct. 15, 1988;141(8):2855-60.
Basham, et al. Synergistic antitumor effect of interferon and anti-idiotype monoclonal antibody in murine lymphoma. J Immunol. Nov. 1, 1986;137(9):3019-24.
Berinstein, et al. Specific enhancement of the therapeutic effect of anti-idiotype antibodies on a murine B cell lymphoma by IL-2. J Immunol. Apr. 15, 1988;140(8):2839-45.
Boyd, et al. Measurement and clinical monitoring of human lymphocyte clonality by massively parallel VDJ pyrosequencing. Sci Transl Med. Dec. 23, 2009;1(12):12ra23.
Brown, et al. Immunoglobulin secretion by mouse X human hybridomas: an approach for the production of anti-idiotype reagents useful in monitoring patients with B cell lymphoma. J Immunol. Sep. 1980;125(3):1037-43.
Brown, et al. Treatment of B-cell lymphomas with anti-idiotype antibodies alone and in combination with alpha interferon. Blood. Feb. 15, 1989;73(3):651-61.
Campbell, et al. Influence of avidity and idiotope recognition on the modulation of surface immunoglobulin on malignant human B cells by rat monoclonal anti-idiotype antibodies. J Immunol. Apr. 15, 1986;136(8):2983-8.

(Continued)

*Primary Examiner* — Jessica H Roark
(74) *Attorney, Agent, or Firm* — Womble Bond Dickinson (US) LLP; Danielle L. Herritt; Cristin H. Cowles

(57) ABSTRACT

The present disclosure relates to therapies for the treatment of tumor, autoimmune diseases, or other diseases. In some embodiments, the present disclosure can relate to subject-specific selection of humanized antibodies targeting clonal lineage specific marker proteins.

9 Claims, 6 Drawing Sheets

(56) References Cited

OTHER PUBLICATIONS

Cohen, Stanley B. Targeting the B Cell in Rheumatoid Arthritis. Best Practice & Research Clinical Rheumatology. vol. 24, Issue 4, Aug. 2010, pp. 553-563. DOI: http://dx.doi.org/10.1016/j.berh.2009.11.006.
Conese, et al. Gene therapy progress and prospects: episomally maintained self-replicating systems. Gene Ther. Dec. 2004;11(24):1735-41.
Damle, et al. Ig V gene mutation status and CD38 expression as novel prognostic indicators in chronic lymphocytic leukemia. Blood. Sep. 15, 1999;94(6):1840-7.
Daniel, et al. Immunotherapy of B-Cell Lymphoma With CD3x19 Bispecific Antibodies: Costimulation via CD28 Prevents "Veto" Apoptosis of Antibody-Targeted Cytotoxic T Cells. Blood 1998 92:4750-4757.
Davis, et al. Anti-idiotype antibodies can induce long-term complete remissions in non-Hodgkin's lymphoma without eradicating the malignant clone. Blood. Aug. 15, 1998;92(4):1184-90.
De Jonge, et al. Bispecific antibody treatment of murine B cell lymphoma. Cancer Immunol Immunother. Nov.-Dec. 1997;45(3-4):162-5.
De Jonge, et al. In vivo retargeting of T cell effector function by recombinant bispecific single chain Fv (anti-CD3 x anti-idiotype) induces long-term survival in the murine BCL1 lymphoma model. J Immunol. Aug. 1, 1998;161(3):1454-61.
De Jonge, et al. Production and characterization of bispecific single-chain antibody fragments. Mol Immunol. Dec. 1995;32(17-18):1405-12.
Demanet, et al. Bispecific antibody-mediated immunotherapy of the BCL1 lymphoma: increased efficacy with multiple injections and CD28-induced costimulation. Blood. May 15, 1996;87(10):4390-8.
Demanet, et al. In vivo studies using bispecific antibodies (anti-CD3 x anti-idiotype) and CD28-induced costimulation in the BCL1 lymphoma. J Hematother. Oct. 1995;4(5):363-8.
Haimovich, et al. Determination of anti-idiotype antibodies by surface plasmon resonance. Journal of Immunological Methods 214(1-2):113-9. Jun. 1998. DOI: 10.1016/S0022-1759(98)00051-9.
Hamblin, et al. Unmutated Ig V(H) genes are associated with a more aggressive form of chronic lymphocytic leukemia. Blood. Sep. 15, 1999;94(6):1848-54.
Hatzubai, et al. The use of a monoclonal anti-idiotype antibody to study the biology of a human B cell lymphoma. J Immunol. Jun. 1981;126(6):2397-402.
International Search Report and Written Opinion dated Dec. 12, 2016 for International PCT Patent Application No. PCT/US2016/051120.
Kaminski, et al. Importance of antibody isotype in monoclonal anti-idiotype therapy of a murine B cell lymphoma. A study of hybridoma class switch variants. J Immunol. Feb. 1, 1986;136(3):1123-30.
Kipps, et al. Developmentally restricted immunoglobulin heavy chain variable region gene expressed at high frequency in chronic lymphocytic leukemia. Proc Natl Acad Sci U S A. Aug. 1989;86(15):5913-7.
Kontermann, Roland E. Dual targeting strategies with bispecific antibodies. MAbs. Mar.-Apr. 2012; 4(2): 182-197. Published online Mar. 1, 2012. doi: 10.4161/mabs.4.2.19000.
Lewis, et al. Surface and cytoplasmic immunoglobulin expression in B-cell chronic lymphocytic leukemia (CLL). Exp Mol Pathol. Oct. 2005;79(2):146-50.
Lowder, et al. Studies on B lymphoid tumors treated with monoclonal anti-idiotype antibodies: correlation with clinical responses. Blood. Jan. 1987;69(1):199-210.
Maloney, et al. Monoclonal anti-idiotype antibodies against the murine B cell lymphoma 38C13: characterization and use as probes for the biology of the tumor in vivo and in vitro. Hybridoma. 1985 Fall;4(3):191-209.
Maloney, et al. Monoclonal anti-idiotype antibody therapy of B-cell lymphoma: the addition of a short course of chemotherapy does not interfere with the antitumor effect nor prevent the emergence of idiotype-negative variant cells. Blood. Sep. 15, 1992;80(6):1502-10.
Matthews, et al. Routine analysis of IgVH mutational status in CLL patients using BIOMED-2 standardized primers and protocols. Leuk Lymphoma. Sep. 2004;45(9):1899-904.
Matutes, et al. The immunological profile of B-cell disorders and proposal of a scoring system for the diagnosis of CLL. Leukemia. Oct. 1994;8(10):1640-5.
Meeker, et al. A clinical trial of anti-idiotype therapy for B cell malignancy. Blood. Jun. 1985;65(6):1349-63.
Meeker, et al. Emergence of Idiotype Variants during Treatment of B-Cell Lymphoma with Anti-Idiotype Antibodies. N Engl J Med 1985; 312:1658-1665. Jun. 27, 1985. DOI: 10.1056/NEJM198506273122602.
Miller, et al. Treatment of B-cell lymphoma with monoclonal anti-idiotype antibody. N Engl J Med. Mar. 4, 1982;306(9):517-22.
Milone, et al. Chimeric receptors containing CD137 signal transduction domains mediate enhanced survival of T cells and increased antileukemic efficacy in vivo. Mol Ther. Aug. 2009;17(8):1453-64. doi: 10.1038/mt.2009.83. Epub Apr. 21, 2009.
Molhoj, et al. CD19-/CD3-bispecific antibody of the BiTE class is far superior to tandem diabody with respect to redirected tumor cell lysis. Mol Immunol. Mar. 2007;44(8):1935-43. Epub Nov. 2, 2006.
Needleman, et al. A general method applicable to the search for similarities in the amino acid sequence of two proteins. J Mol Biol. Mar. 1970;48(3):443-53.
Parameswaran, et al. Convergent antibody signatures in human dengue. Cell Host Microbe. Jun. 12, 2013;13(6):691-700. doi: 10.1016/j.chom.2013.05.008.
Pearson, et al. Improved tools for biological sequence comparison. Proc Natl Acad Sci U S A. Apr. 1988;85(8):2444-8.
Pezzella, et al. Expression of the bcl-2 oncogene protein is not specific for the 14;18 chromosomal translocation. Am J Pathol. Aug. 1990;137(2):225-32.
Rader, Christoph. DARTs take aim at BiTEs. Blood 2011 117:4403-4404; doi:10.1182/blood-2011-02-337691.
Renschler, et al. Synthetic peptide ligands of the antigen binding receptor induce programmed cell death in a human B-cell lymphoma. Proc Natl Acad Sci U S A. Apr. 26, 1994;91(9):3623-7.
Schatz, et al. Biochemistry of V(D)J recombination. Curr Top Microbiol Immunol. 2005;290:49-85.
Schlissel, Mark S. Regulating antigen-receptor gene assembly. Nat Rev Immunol. Nov. 2003;3(11):890-9.
Shalaby, et al. Development of humanized bispecific antibodies reactive with cytotoxic lymphocytes and tumor cells overexpressing the HER2 protooncogene. J Exp Med. Jan. 1, 1992;175(1):217-25.
Smith, et al. A novel, native-format bispecific antibody triggering T-cell killing of B-cells is robustly active in mouse tumor models and cynomolgus monkeys. Scientific Reports 5, Article No. 17943. (2015). Published online:Dec. 11, 2015. doi:10.1038/srep17943.
Smith, et al. Comparison of Biosequences. Advances in Applied Mathematics. vol. 2, Issue 4, Dec. 1981, pp. 482-489. doi:10.1016/0196-8858(81)90046-4.
Smith, et al. FcγRIIB in autoimmunity and infection: evolutionary and therapeutic implications. Nat Rev Immunol. May 2010; 10(5): 328-343. Nat Rev Immunol. Author manuscript; available in PMC Aug. 29, 2014.
Sun, et al. Anti-CD20/CD3 T cell-dependent bispecific antibody for the treatment of B cell malignancies. Sci Transl Med. May 13, 2015;7(287):287ra70. doi: 10.1126/scitranslmed.aaa4802.
Thielemans, et al. Strategies for production of monoclonal anti-idiotype antibodies against human B cell lymphomas. J Immunol. Jul. 1984;133(1):495-501.
Torchia, et al. Semi-synthetic peptibodies are a novel personalized therapeutic with activity against lymphoma in vitro and in vivo. Stanford School of Medicine. 2014 AACR poster #2690. 1 page.
Torchia, et al. Targeting lymphoma with precision using semisynthetic anti-idiotype peptibodies. Proc Natl Acad Sci U S A. May 10, 2016;113(19):5376-81. doi:10.1073/pnas.1603335113. Epub Apr. 25, 2016.

(56) References Cited

OTHER PUBLICATIONS

Tsakou, et al. Partial versus productive immunoglobulin heavy locus rearrangements in chronic lymphocytic leukemia: implications for B-cell receptor stereotypy. Mol Med. Feb. 10, 2012;18:138-45. doi: 10.2119/molmed.2011.00216.

Tsakou, et al. Supplemental Data. Partial versus productive immunoglobulin heavy locus rearrangements in chronic lymphocytic leukemia: implications for B-cell receptor stereotypy. Mol Med. 2012. S1-S7.

Urlaub, et al. Isolation of Chinese hamster cell mutants deficient in dihydrofolate reductase activity. Proc Natl Acad Sci U S A. Jul. 1980; 77(7): 4216-4220.

Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.

Varghese, et al. Generation of CD8+ T cell-mediated immunity against idiotype-negative lymphoma escapees. Blood. Nov. 12, 2009;114(20):4477-85. doi: 10.1182/blood-2009-05-223263. Epub Sep. 17, 2009.

Veri, et al. Therapeutic control of B cell activation via recruitment of Fcgamma receptor IIb (CD32B) inhibitory function with a novel bispecific antibody scaffold. Arthritis Rheum. Jul. 2010;62(7):1933-43. doi: 10.1002/art.27477.

Warnke, et al. Detection of T and B cell antigens hybridoma monoclonal antibodies: a biotin-avidin-horseradish peroxidase method. J Histochem Cytochem. Aug. 1980;28(8):771-6.

Ye, et al. IgBLAST: an immunoglobulin variable domain sequence analysis tool. Nucleic Acids Res. Jul. 2013;41(Web Server issue):W34-40. doi: 10.1093/nar/gkt382. Epub May 13, 2013.

Zomas, et al. Expression of the immunoglobulin-associated protein B29 in B cell disorders with the monoclonal antibody SN8 (CD79b). Leukemia. Dec. 1996;10(12):1966-70.

\* cited by examiner

METHOD OF MAKING PATIENT SPECIFIC ANTI-IDIOTYPE ANTIBODIES

CROSS-REFERENCE

The present application is a non-provisional of, and claims the benefit of U.S. Provisional Patent Application No. 62/216,992 filed on Sep. 10, 2015, the entire contents of which are incorporated herein by reference.

BACKGROUND

The use of humanized tumor-targeting molecules in cancer therapeutics has seen remarkable success in recent years. In particular, antibody-based therapies have proven to be an important strategy for treating patients with hematological malignancies and tumors. However, current treatments can also provoke immune reactions against a wide range of normal cells (e.g., a patient's B lymphocytes), resulting in serious side effects. Thus, an immediate clinical need exists for cancer therapeutics with increased targeting selectivity (e.g., the ability to selectively target cancer cells). The present disclosure provides safer and less toxic compositions and methods for cancer therapy that overcome the limitations of conventional therapies.

BRIEF SUMMARY

This disclosure provides compositions and methods. In some aspects, this disclosure provides a humanized construct. In some embodiments, the humanized construct can comprise a first domain. In some embodiments, the humanized construct can comprise a first domain having an affinity for a clonal lineage specific marker protein (CLSMP). In some embodiments, the humanized construct can comprise a second domain. In some embodiments, the humanized construct can comprise a second domain having an affinity for an effector antigen. In some embodiments, the effector antigen can be CD3, CD28, CTLA4, PD-1, IL-2R, or Fc receptor. In some embodiments, the humanized construct can comprise a third domain. In some embodiments, the humanized construct can comprise a third domain having an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, and FMC7. In some embodiments, the humanized construct can comprise a humanized anti-neoepitope agent (ANA). In some embodiments, the humanized construct can comprise a humanized monoclonal antibody or fragment thereof. In some embodiments, the humanized construct can comprise a first domain, and the first domain can comprise a humanized antibody fragment selected from the group consisting of a fragment antigen-binding (fAb) domain and a single chain variable fragment (scFv) domain. In some embodiments, the humanized construct can comprise a humanized antibody fragment, and the humanized antibody fragment is selected from a complex library comprising a plurality of humanized antibody fragments. In some embodiments, the humanized construct can comprise an fAb domain, and the complex library can comprise a phagemid display library comprising a plurality of phage expressing fAb domains. In some embodiments, the humanized construct can comprise an scFv domain, and the complex library can comprise an scFv library comprising a plurality of scFv domains. In some embodiments, the humanized construct can comprise a first domain having an affinity for a clonal lineage specific marker protein (CLSMP), and the CLSMP can be at least in part derived from a gene, and the gene can be IGHV1-69, IGHV1-2, IGHV4-39, IGHV3-30, IGHV4-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, IGHV7-4, or any gene fragment thereof. In some embodiments, the humanized construct can comprise a first domain having an affinity for a CLSMP, and the CLSMP is at least in part derived from a gene selected from a gene class. In some embodiments, the gene class can be IGHV1, IGHV2, IGHV3, IGHV4, IGHV5, IGHV6, or IGHV7. In some embodiments, the humanized construct can comprise a first domain having an affinity for a CLSMP, and the CLSMP can comprise a B cell receptor (BCR) idiotype. In some embodiments, the CLSMP can comprise a B cell receptor (BCR) idiotype, and the BCR idiotype can comprise an IGHV gene product associated with at least one of an IGLV gene product or an IGKV gene product. In some embodiments, the humanized construct can comprise a first domain having an affinity for a CLSMP, and the CLSMP corresponds to a T cell receptor (TCR) idiotype. In some embodiments, the humanized construct can comprise a first domain having an affinity for a CLSMP, and the CLSMP can comprise a tumor neo-epitope, a tumor-specific antigen, a tumor-associated antigen, or a lineage-specific protein alteration. In some embodiments, the humanized construct can comprise a first domain having an affinity for a CLSMP, and the CLSMP is located on one or more cells. In some embodiments, one or more cells comprise tumor cells. In some embodiments, one or more cells comprise tumor cells, and the tumor cells comprise malignant B cells. In some embodiments, the malignant B cells can be lymphocytic leukemia (CLL) cells, acute lymphocytic leukemia (ALL) cells, acute myeloid leukemia (AML) cells, mantle cell lymphoma (MCL) cells, diffuse large B cell lymphoma (DLBCL) cells, or follicular lymphoma (FL) cells. In some embodiments, one or more cells comprise tumor cells, and the tumor cells comprise malignant T cells. In some embodiments, the malignant T cells comprise lymphocytic cells, or leukemia cells. In some embodiments, the one or more cells may correspond to an autoimmune disease. In some embodiments, the autoimmune disease can be Type I diabetes, Sjögren's syndrome, or rheumatoid arthritis.

In some aspects, this disclosure provides a library comprising a plurality of humanized polypeptides. In some embodiments, each of the plurality of humanized polypeptides can independently comprise a first domain. In some embodiments, the first domain can have an affinity for a clonal lineage specific marker protein (CLSMP). In some embodiments, each of the plurality of humanized polypeptides can independently comprise a second domain. In some embodiments, the second domain can have an affinity for an effector antigen. In some embodiments, the effector antigen can be CD3, CD28, CTLA4, PD-1, IL-2R, or Fc receptor. In some embodiments, each of the plurality of humanized polypeptides can further comprise a third domain. In some embodiments, the third domain can have an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, or FMC7.

In some aspects, the present disclosure provides a humanized construct prepared by a process comprising obtaining a biological sample from a subject having a disease. In some embodiments, the biological sample can comprise disease-derived cells. In some embodiments, the present disclosure provides a humanized construct prepared by a process comprising sequencing one or more nucleic acids from the biological sample, thereby producing a plurality of sequence reads. In some embodiments, the present disclosure provides a humanized construct prepared by a process comprising determining the sequence corresponding to a clonal lineage specific marker protein (CLSMP). In some embodiments, the step of determining may be performed using a computer system. In some embodiments, the CLSMP may be expressed by a disease-derived cell. In some embodiments, the determining may be performed using the plurality of sequence reads. In some embodiments, the present disclosure provides a humanized construct prepared by a process comprising identifying an antibody fragment having an affinity for the CLSMP. In some embodiments, the present disclosure provides a humanized construct prepared by a process comprising making a humanized construct comprising the identified antibody fragment identified and an effector domain having an affinity for an effector antigen. In some embodiments, the effector antigen can be CD3, CD28, CTLA4, PD-1, IL-2R, or Fc receptor. In some embodiments, a subject can have a disease, and the disease can be chronic lymphocytic leukemia (CLL), acute lymphocytic leukemia (ALL), acute myeloid leukemia (AML), mantle cell lymphoma (MCL), diffuse large B cell lymphoma (DLBCL), or follicular lymphoma (FL) cells. In some embodiments, the disease-derived cells can comprise malignant B cells. In some embodiments, a subject can have a disease, and the disease can be T cell lymphoma or T cell leukemia. In some embodiments, the disease-derived cells can comprise malignant T cells. In some embodiments, a subject can have a disease, and the disease can be an autoimmune disease. In some embodiments, the autoimmune disease can be Type I diabetes, Sjögren's syndrome, or rheumatoid arthritis. In some embodiments, the sequencing can comprises next generation sequencing. In some embodiments, identifying the antibody fragment having an affinity for the CLSMP can comprise expressing the CLSMP as a protein using the determined sequence corresponding to the CLSMP. In some embodiments, identifying the antibody fragment having an affinity for the CLSMP can comprise immobilizing the protein or a fragment thereof on a substrate. In some embodiments, identifying the antibody fragment having an affinity for the CLSMP can comprise contacting each of a plurality of humanized antibody fragments selected from a complex library to the immobilized protein of to identify the antibody fragment having an affinity for the CLSMP. In some embodiments, the plurality of humanized antibody fragments can comprise fragment antigen binding (fAb) domains. In some embodiments, the complex library can comprises a phagemid display library comprising a plurality of phage expressing fAb domains. In some embodiments, the plurality of humanized antibody fragments can comprise single chain variable fragment (scFv) domains. In some embodiments, the complex library can comprise a scFv library comprising a plurality of scFv domains. In some embodiments, preparing the humanized construct can comprise producing an antibody comprising the identified fAb domain using a hybridoma. In some embodiments, preparing the humanized construct can comprise ligating the effector domain to the antibody comprising the fAb domain, or a fragment of the antibody thereof, thereby preparing the humanized construct. In some embodiments, the present disclosure provides a humanized construct prepared by a process, and the process can comprise ligating to the antibody comprising the fAb domain, or a fragment of the antibody thereof, a cell surface antigen (CSA) domain. In some embodiments, the CSA domain can have an affinity for an antigen, and the antigen can be CD3, CD4, CD5, CD8, CD19, CD20, CD22, CD23, CD28, CD38, CD45RA, CD45RO, CD79a, CD79b, CD97, or FMC7. In some embodiments, the humanized construct can comprise a humanized anti-neoepitope agent (ANA). In some embodiments, the humanized construct can comprise a humanized monoclonal antibody or fragment thereof. In some embodiments, the CLSMP can be at least in part derived from a gene. In some embodiments, the gene can be IGHV1-69, IGHV1-2, IGHV4-39, IGHV3-30, IGHV4-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, IGHV7-4, or any gene fragment thereof. In some embodiments, the CLSMP can be at least in part derived from a gene selected from a gene class. In some embodiments, the gene class can be IGHV1, IGHV2, IGHV3, IGHV4, IGHV5, IGHV6, or IGHV7. In some embodiments, the CLSMP can comprise a B cell receptor (BCR) idiotype. In some embodiments, the BCR idiotype can comprise an IGHV gene product associated with at least one of an IGLV gene product or an IGKV gene product. In some embodiments, the CLSMP can comprise a T cell receptor (TCR) idiotype. In some embodiments, the CLSMP can comprise a tumor neo-epitope, a tumor-specific antigen, a tumor-associated antigen, or a lineage-specific protein alteration.

In some aspects, the present disclosure provides a nucleic acid molecule encoding a humanized construct. In some embodiments, the nucleic acid molecule encoding the humanized construct can comprise a first sequence. In some embodiments, the first sequence can encode a first domain. In some embodiments, the first domain can have an affinity for a clonal lineage specific marker protein (CLSMP). In some embodiments, the nucleic acid molecule encoding the humanized construct can comprise a second sequence. In some embodiments, the second sequence can encode a second domain. In some embodiments, the second domain can having an affinity for an effector antigen. In some embodiments, the effector antigen can be CD3, CD28, CTLA4, PD-1, IL-2R, or Fc receptor. In some embodiments, the nucleic acid molecule encoding the humanized construct can comprise a third sequence. In some embodiments, the third sequence can encode a third domain having an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, or FMC7. In some embodiments, the humanized construct can comprise a humanized anti-neoepitope agent (ANA). In some embodiments, the humanized construct can comprise a humanized monoclonal antibody or fragment thereof. In some embodiments, the humanized construct can comprise a first domain, and the first domain can comprise a humanized antibody fragment selected from the group consisting of a fragment antigen-binding (fAb) domain and a single chain variable fragment (scFv) domain. In some embodiments, the humanized construct can comprise a humanized antibody fragment, and the humanized antibody fragment is selected from a complex library comprising a plurality of humanized antibody fragments. In some embodiments, the humanized construct can comprise an fAb domain, and the complex library can comprise a phagemid display library comprising a plurality of phage expressing fAb domains. In some embodiments, the humanized construct can comprise an scFv domain, and the complex library can comprise an scFv library comprising a plurality of scFv domains. In some embodiments, the humanized construct can comprise a first domain having an affinity for a clonal lineage specific marker protein (CLSMP), and the CLSMP can be at least in part derived from a gene, and the gene can be IGHV1-69, IGHV1-2, IGHV4-39, IGHV3-30, IGHV4-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, IGHV7-4, or any gene fragment thereof. In some embodiments, the humanized construct can comprise a first domain having an affinity for a CLSMP, and the CLSMP is at least in part derived from a gene selected from a gene class. In some embodiments, the gene class can be IGHV1, IGHV2, IGHV3, IGHV4, IGHV5, IGHV6, or IGHV7. In some embodiments, the humanized construct can comprise a first domain having an affinity for a CLSMP, and the CLSMP can comprise a B cell receptor (BCR) idiotype. In some embodiments, the CLSMP can comprise a B cell receptor (BCR) idiotype, and the BCR idiotype can comprise an IGHV gene product associated with at least one of an IGLV gene product or an IGKV gene product. In some embodiments, the humanized construct can comprise a first domain having an affinity for a CLSMP, and the CLSMP corresponds to a T cell receptor (TCR) idiotype. In some embodiments, the humanized construct can comprise a first domain having an affinity for a CLSMP, and the CLSMP can comprise a tumor neo-epitope, a tumor-specific antigen, a tumor-associated antigen, or a lineage-specific protein alteration. In some embodiments, the humanized construct can comprise a first domain having an affinity for a CLSMP, and the CLSMP is located on one or more cells. In some embodiments, one or more cells comprise tumor cells. In some embodiments, one or more cells comprise tumor cells, and the tumor cells comprise malignant B cells. In some embodiments, the malignant B cells can be lymphocytic leukemia (CLL) cells, acute lymphocytic leukemia (ALL) cells, acute myeloid leukemia (AML) cells, mantle cell lymphoma (MCL) cells, diffuse large B cell lymphoma (DLBCL) cells, or follicular lymphoma (FL) cells. In some embodiments, one or more cells comprise tumor cells, and the tumor cells comprise malignant T cells. In some embodiments, the malignant T cells comprise lymphocytic cells, or leukemia cells. In some embodiments, the one or more cells may correspond to an autoimmune disease. In some embodiments, the autoimmune disease can be Type I diabetes, Sjögren's syndrome, or rheumatoid arthritis. In some embodiments, the nucleic acid can comprise deoxyribonucleic acid (DNA), ribonucleic acid (RNA), or a hybrid thereof. In some embodiments, the nucleic acid can comprise a barcode sequence. In some embodiments, the barcode sequence can comprise between about 1 and about 50 nucleotides. In some embodiments, the barcode sequence can uniquely identify the humanized construct encoded by the nucleic acid.

In some aspects, this disclosure provides a library comprising a plurality of humanized polynucleotides. In some embodiments, each of the plurality of humanized polynucleotides can independently comprise a first sequence. In some embodiments, the first sequence can encode a first domain having an affinity for a clonal lineage specific marker protein (CLSMP). In some embodiments, each of the plurality of humanized polynucleotides can independently comprise a second sequence. In some embodiments, the second sequence can encode a second domain having an affinity for an effector antigen. In some embodiments, the effector antigen can be CD3, CD28, CTLA4, PD-1, IL-2R, or Fc receptor. In some embodiments, each of the plurality of humanized polynucleotides can further comprise a third sequence. In some embodiments, the third sequence can encode a third domain having an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, or FMC7.

In some aspects, the present disclosure provides a method comprising obtaining a biological sample from a subject having a disease, the biological sample comprising normal cells and potentially disease-derived cells. In some embodiments, the present disclosure provides a method comprising enriching the biological sample for a plurality of cells comprising a clonal lineage specific marker protein (CLSMP). In some embodiments, the present disclosure provides a method comprising sequencing a plurality of amplicons prepared from the enriched plurality of cells, thereby generating a first sequence analysis. In some embodiments, the present disclosure provides a method comprising comparing, using a computer, the first sequence analysis to a reference. In some embodiments, the present disclosure provides a method comprising selecting a humanized construct for treatment of the disease in the subject based on the comparison. In some embodiments, the sequencing can comprise performing reverse transcription on a plurality of RNA molecules corresponding to the CLSMP expressed in the enriched plurality of cells, thereby generating a plurality of cDNA molecules. In some embodiments, the sequencing can comprise amplifying the plurality of cDNA molecules, thereby generating a plurality of amplicons. In some embodiments, the sequencing can comprise sequencing the plurality of amplicons, thereby generating a plurality of sequence reads. In some embodiments, the sequencing can comprise non-Sanger-based sequencing. In some embodiments, the sequencing can comprise clustering the plurality of sequence reads by similarity to generate a set of cluster-representative sequences. In some embodiments, the comparing can comprise aligning the set of cluster-representative sequences to the reference. In some embodiments, the comparing can comprise rank ordering the set of cluster-representative sequences by abundance. In some embodiments, the comparing can comprise determining a most abundant CLSMP expressed in the enriched plurality of cells. In some embodiments, the reference can correspond to a second sequence analysis generated by sequencing a second plurality of nucleic acid molecules prepared from a reference biological sample from the subject, wherein the reference biological sample can comprise a second plurality of cells, and wherein the reference biological sample is not enriched for a plurality of cells comprising the CLSMP. In some embodiments, selecting the humanized construct can be based on the most abundant CLSMP expressed in the enriched plurality of cells. In some embodiments, selecting the humanized construct can comprise screening a library comprising a plurality of different humanized constructs, and selecting the humanized construct. In some embodiments, the humanized construct can comprise a first domain having an affinity for the CLSMP. In some embodiments, the humanized construct can comprise a second domain having an affinity for an effector antigen. In some embodiments, the effector antigen can be CD3, CD28, CTLA4, PD-1, IL-2R, or Fc receptor. In some embodiments, the humanized construct further can comprise a third domain. In some embodiments, the third domain can have an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, or FMC7. In some embodiments, the humanized construct can comprise a humanized anti-neoepitope agent (ANA). In some embodiments, the humanized construct can comprise a humanized monoclonal antibody or fragment thereof. In some embodiments, the humanized construct can comprise a first domain, and the first domain can comprise a humanized antibody fragment selected from the group consisting of a fragment antigen-binding (fAb) domain and a single chain variable fragment (scFv) domain. In some embodiments, the humanized construct can comprise a humanized antibody fragment, and the humanized antibody fragment is selected from a complex library comprising a plurality of humanized antibody fragments. In some embodiments, the humanized construct can comprise an fAb domain, and the complex library can comprise a phagemid display library comprising a plurality of phage expressing fAb domains. In some embodiments, the humanized construct can comprise an scFv domain, and the complex library can comprise an scFv library comprising a plurality of scFv domains. In some embodiments, the humanized construct can comprise a first domain having an affinity for a clonal lineage specific marker protein (CLSMP), and the CLSMP can be at least in part derived from a gene, and the gene can be IGHV1-69, IGHV1-2, IGHV4-39, IGHV3-30, IGHV4-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, IGHV7-4, or any gene fragment thereof. In some embodiments, the humanized construct can comprise a first domain having an affinity for a CLSMP, and the CLSMP is at least in part derived from a gene selected from a gene class. In some embodiments, the gene class can be IGHV1, IGHV2, IGHV3, IGHV4, IGHV5, IGHV6, or IGHV7. In some embodiments, the humanized construct can comprise a first domain having an affinity for a CLSMP, and the CLSMP can comprise a B cell receptor (BCR) idiotype. In some embodiments, the CLSMP can comprise a B cell receptor (BCR) idiotype, and the BCR idiotype can comprise an IGHV gene product associated with at least one of an IGLV gene product or an IGKV gene product. In some embodiments, the humanized construct can comprise a first domain having an affinity for a CLSMP, and the CLSMP corresponds to a T cell receptor (TCR) idiotype. In some embodiments, the humanized construct can comprise a first domain having an affinity for a CLSMP, and the CLSMP can comprise a tumor neo-epitope, a tumor-specific antigen, a tumor-associated antigen, or a lineage-specific protein alteration. In some embodiments, the humanized construct can comprise a first domain having an affinity for a CLSMP, and the CLSMP is located on one or more cells. In some embodiments, one or more cells comprise tumor cells. In some embodiments, one or more cells comprise tumor cells, and the tumor cells comprise malignant B cells. In some embodiments, the malignant B cells can be lymphocytic leukemia (CLL) cells, acute lymphocytic leukemia (ALL) cells, acute myeloid leukemia (AML) cells, mantle cell lymphoma (MCL) cells, diffuse large B cell lymphoma (DLBCL) cells, or follicular lymphoma (FL) cells. In some embodiments, one or more cells comprise tumor cells, and the tumor cells comprise malignant T cells. In some embodiments, the malignant T cells comprise lymphocytic cells, or leukemia cells. In some embodiments, the one or more cells may correspond to an autoimmune disease. In some embodiments, the autoimmune disease can be Type I diabetes, Sjögren's syndrome, or rheumatoid arthritis. In some embodiments, the method can further comprise administering to the subject the selected humanized construct. In some embodiments, the method can further comprise administering to the subject an anti-cancer therapy or a radiation therapy.

In some aspects, the present disclosure provides a genetically modified cell expressing a humanized construct. In some embodiments, the humanized construct can comprise a first domain. In some embodiments, the first domain can have an affinity for a clonal lineage specific marker protein (CLSMP). In some embodiments, the humanized construct can comprise a second domain. In some embodiments, the second domain can have an affinity for an effector antigen selected from the group consisting of CD3, CD28, CTLA4, PD-1, IL-2R, or Fc receptor. In some embodiments, the humanized construct can further comprise a third domain. In some embodiments, the third domain can have an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, or FMC7. In some embodiments, the genetically modified cell can comprise a cytotoxic T lymphocyte. In some embodiments, the humanized construct can comprise a humanized anti-neoepitope agent (ANA). In some embodiments, the humanized construct can comprise a humanized monoclonal antibody or fragment thereof. In some embodiments, the humanized construct can comprise a first domain, and the first domain can comprise a humanized antibody fragment selected from the group consisting of a fragment antigen-binding (fAb) domain and a single chain variable fragment (scFv) domain. In some embodiments, the humanized construct can comprise a humanized antibody fragment, and the humanized antibody fragment is selected from a complex library comprising a plurality of humanized antibody fragments. In some embodiments, the humanized construct can comprise an fAb domain, and the complex library can comprise a phagemid display library comprising a plurality of phage expressing fAb domains. In some embodiments, the humanized construct can comprise an scFv domain, and the complex library can comprise an scFv library comprising a plurality of scFv domains. In some embodiments, the humanized construct can comprise a first domain having an affinity for a clonal lineage specific marker protein (CLSMP), and the CLSMP can be at least in part derived from a gene, and the gene can be IGHV1-69, IGHV1-2, IGHV4-39, IGHV3-30, IGHV4-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, IGHV7-4, or any gene fragment thereof. In some embodiments, the humanized construct can comprise a first domain having an affinity for a CLSMP, and the CLSMP is at least in part derived from a gene selected from a gene class. In some embodiments, the gene class can be IGHV1, IGHV2, IGHV3, IGHV4, IGHV5, IGHV6, or IGHV7. In some embodiments, the humanized construct can comprise a first domain having an affinity for a CLSMP, and the CLSMP can comprise a B cell receptor (BCR) idiotype. In some embodiments, the CLSMP can comprise a B cell receptor (BCR) idiotype, and the BCR idiotype can comprise an IGHV gene product associated with at least one of an IGLV gene product or an IGKV gene product. In some embodiments, the humanized construct can comprise a first domain having an affinity for a CLSMP, and the CLSMP corresponds to a T cell receptor (TCR) idiotype. In some embodiments, the humanized construct can comprise a first domain having an affinity for a CLSMP, and the CLSMP can comprise a tumor neo-epitope, a tumor-specific antigen, a tumor-associated antigen, or a lineage-specific protein alteration. In some embodiments, the humanized construct can comprise a first domain having an affinity for a CLSMP, and the CLSMP is located on one or more cells. In some embodiments, one or more cells comprise tumor cells. In some embodiments, one or more cells comprise tumor cells, and the tumor cells comprise malignant B cells. In some embodiments, the malignant B cells can be lymphocytic leukemia (CLL) cells, acute lymphocytic leukemia (ALL) cells, acute myeloid leukemia (AML) cells, mantle cell lymphoma (MCL) cells, diffuse large B cell lymphoma (DLBCL) cells, or follicular lymphoma (FL) cells. In some embodiments, one or more cells comprise tumor cells, and the tumor cells comprise malignant T cells. In some embodiments, the malignant T cells comprise lymphocytic cells, or leukemia cells. In some embodiments, the one or more cells may correspond to an autoimmune disease. In some embodiments, the autoimmune disease can be Type I diabetes, Sjögren's syndrome, or rheumatoid arthritis.

In some aspects, the present disclosure provides a humanized construct for use as a medicament. In some embodiments, the humanized construct can comprise a first domain. In some embodiments, the humanized construct can comprise a first domain having an affinity for a clonal lineage specific marker protein (CLSMP). In some embodiments, the humanized construct can comprise a second domain. In some embodiments, the humanized construct can comprise a second domain having an affinity for an effector antigen. In some embodiments, the effector antigen can be CD3, CD28, CTLA4, PD-1, IL-2R, or Fc receptor. In some embodiments, the humanized construct can comprise a third domain. In some embodiments, the humanized construct can comprise a third domain having an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, and FMC7. In some embodiments, the humanized construct can comprise a humanized anti-neoepitope agent (ANA). In some embodiments, the humanized construct can comprise a humanized monoclonal antibody or fragment thereof. In some embodiments, the humanized construct can comprise a first domain, and the first domain can comprise a humanized antibody fragment selected from the group consisting of a fragment antigen-binding (fAb) domain and a single chain variable fragment (scFv) domain. In some embodiments, the humanized construct can comprise a humanized antibody fragment, and the humanized antibody fragment is selected from a complex library comprising a plurality of humanized antibody fragments. In some embodiments, the humanized construct can comprise an fAb domain, and the complex library can comprise a phagemid display library comprising a plurality of phage expressing fAb domains. In some embodiments, the humanized construct can comprise an scFv domain, and the complex library can comprise an scFv library comprising a plurality of scFv domains. In some embodiments, the humanized construct can comprise a first domain having an affinity for a clonal lineage specific marker protein (CLSMP), and the CLSMP can be at least in part derived from a gene, and the gene can be IGHV1-69, IGHV1-2, IGHV4-39, IGHV3-30, IGHV4-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, IGHV7-4, or any gene fragment thereof. In some embodiments, the humanized construct can comprise a first domain having an affinity for a CLSMP, and the CLSMP is at least in part derived from a gene selected from a gene class. In some embodiments, the gene class can be IGHV1, IGHV2, IGHV3, IGHV4, IGHV5, IGHV6, or IGHV7. In some embodiments, the humanized construct can comprise a first domain having an affinity for a CLSMP, and the CLSMP can comprise a B cell receptor (BCR) idiotype. In some embodiments, the CLSMP can comprise a B cell receptor (BCR) idiotype, and the BCR idiotype can comprise an IGHV gene product associated with at least one of an IGLV gene product or an IGKV gene product. In some embodiments, the humanized construct can comprise a first domain having an affinity for a CLSMP, and the CLSMP corresponds to a T cell receptor (TCR) idiotype. In some embodiments, the humanized construct can comprise a first domain having an affinity for a CLSMP, and the CLSMP can comprise a tumor neo-epitope, a tumor-specific antigen, a tumor-associated antigen, or a lineage-specific protein alteration. In some embodiments, the humanized construct can comprise a first domain having an affinity for a CLSMP, and the CLSMP is located on one or more cells. In some embodiments, one or more cells comprise tumor cells. In some embodiments, one or more cells comprise tumor cells, and the tumor cells comprise malignant B cells. In some embodiments, the malignant B cells can be lymphocytic leukemia (CLL) cells, acute lymphocytic leukemia (ALL) cells, acute myeloid leukemia (AML) cells, mantle cell lymphoma (MCL) cells, diffuse large B cell lymphoma (DLBCL) cells, or follicular lymphoma (FL) cells. In some embodiments, one or more cells comprise tumor cells, and the tumor cells comprise malignant T cells. In some embodiments, the malignant T cells comprise lymphocytic cells, or leukemia cells. In some embodiments, the one or more cells may correspond to an autoimmune disease. In some embodiments, the autoimmune disease can be Type I diabetes, Sjögren's syndrome, or rheumatoid arthritis.

In some aspects, the present disclosure provides use of a humanized construct in the manufacture of a medicament. In some embodiments, the humanized construct can comprise a first domain. In some embodiments, the humanized construct can comprise a first domain having an affinity for a clonal lineage specific marker protein (CLSMP). In some embodiments, the humanized construct can comprise a second domain. In some embodiments, the humanized construct can comprise a second domain having an affinity for an effector antigen. In some embodiments, the effector antigen can be CD3, CD28, CTLA4, PD-1, IL-2R, or Fc receptor. In some embodiments, the humanized construct can comprise a third domain. In some embodiments, the humanized construct can comprise a third domain having an affinity for a cell surface antigen. In some embodiments, the cell surface antigen can be CD3, CD4, CD5, CD8, CD19, CD20, CD22, CD23, CD28, CD38, CD45RA, CD45RO, CD79a, CD79b, CD97, and FMC7. In some embodiments, the humanized construct can comprise a humanized antineoepitope agent (ANA). In some embodiments, the humanized construct can comprise a humanized monoclonal antibody or fragment thereof. In some embodiments, the humanized construct can comprise a first domain, and the first domain can comprise a humanized antibody fragment selected from the group consisting of a fragment antigen-binding (fAb) domain and a single chain variable fragment (scFv) domain. In some embodiments, the humanized construct can comprise a humanized antibody fragment, and the humanized antibody fragment is selected from a complex library comprising a plurality of humanized antibody fragments. In some embodiments, the humanized construct can comprise an fAb domain, and the complex library can comprise a phagemid display library comprising a plurality of phage expressing fAb domains. In some embodiments, the humanized construct can comprise an scFv domain, and the complex library can comprise an scFv library comprising a plurality of scFv domains. In some embodiments, the humanized construct can comprise a first domain having an affinity for a clonal lineage specific marker protein (CLSMP), and the CLSMP can be at least in part derived from a gene, and the gene can be IGHV1-69, IGHV1-2, IGHV4-39, IGHV3-30, IGHV3-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, IGHV7-4, or any gene fragment thereof. In some embodiments, the humanized construct can comprise a first domain having an affinity for a CLSMP, and the CLSMP is at least in part derived from a gene selected from a gene class. In some embodiments, the gene class can be IGHV1, IGHV2, IGHV3, IGHV4, IGHV5, IGHV6, or IGHV7. In some embodiments, the humanized construct can comprise a first domain having an affinity for a CLSMP, and the CLSMP can comprise a B cell receptor (BCR) idiotype. In some embodiments, the CLSMP can comprise a B cell receptor (BCR) idiotype, and the BCR idiotype can comprise an IGHV gene product associated with at least one of an IGLV gene product or an IGKV gene product. In some embodiments, the humanized construct can comprise a first domain having an affinity for a CLSMP, and the CLSMP corresponds to a T cell receptor (TCR) idiotype. In some embodiments, the humanized construct can comprise a first domain having an affinity for a CLSMP, and the CLSMP can comprise a tumor neo-epitope, a tumor-specific antigen, a tumor-associated antigen, or a lineage-specific protein alteration. In some embodiments, the humanized construct can comprise a first domain having an affinity for a CLSMP, and the CLSMP is located on one or more cells. In some embodiments, one or more cells comprise tumor cells. In some embodiments, one or more cells comprise tumor cells, and the tumor cells comprise malignant B cells. In some embodiments, the malignant B cells can be lymphocytic leukemia (CLL) cells, acute lymphocytic leukemia (ALL) cells, acute myeloid leukemia (AML) cells, mantle cell lymphoma (MCL) cells, diffuse large B cell lymphoma (DLBCL) cells, or follicular lymphoma (FL) cells. In some embodiments, one or more cells comprise tumor cells, and the tumor cells comprise malignant T cells. In some embodiments, the malignant T cells comprise lymphocytic cells, or leukemia cells. In some embodiments, the one or more cells may correspond to an autoimmune disease. In some embodiments, the autoimmune disease can be Type I diabetes, Sjögren's syndrome, or rheumatoid arthritis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
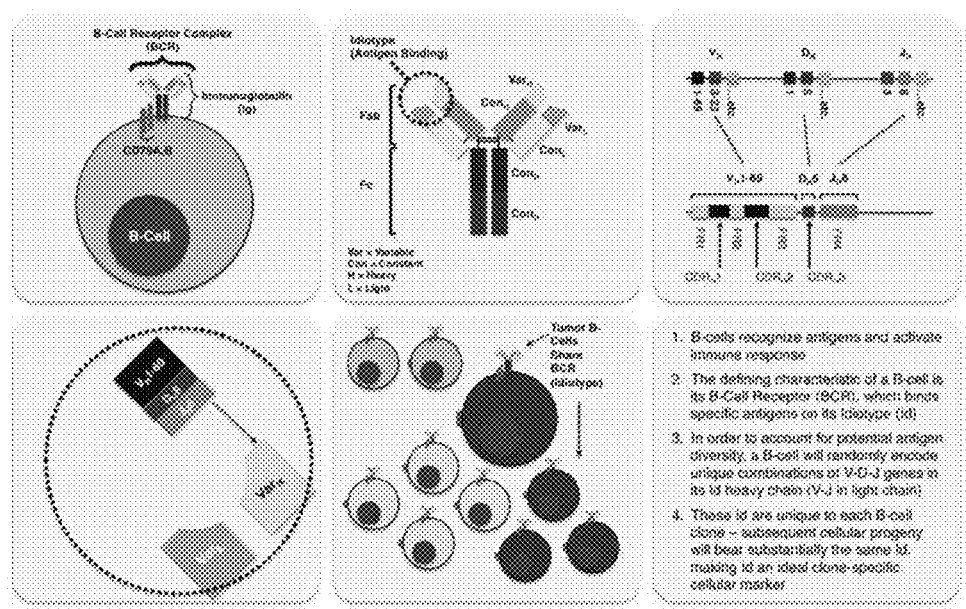
FIG. 1 depicts a brief overview of B cell receptor (BCR) idiotypes.
Figure 2:
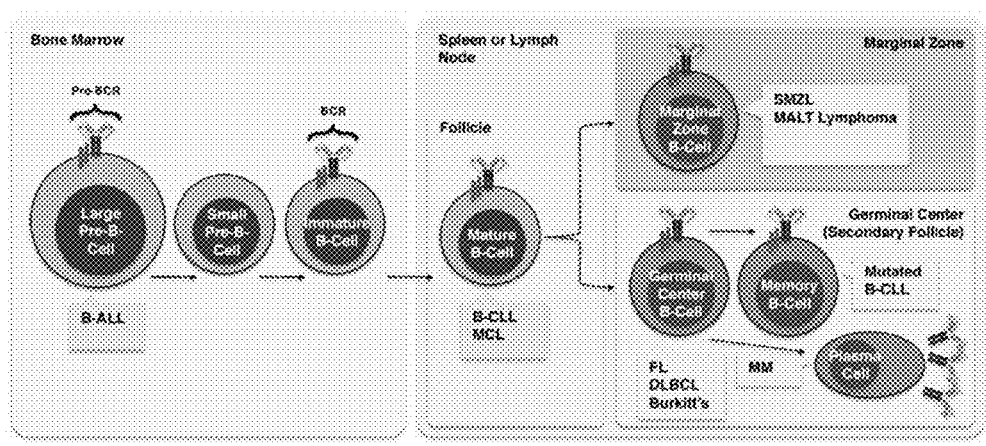
FIG. 2 depicts the pathogenesis of B cell neoplasms.

The compositions and methods provided herein generally relate to humanized antibody therapies suitable for the treatment of cancer and autoimmune diseases. The compositions and methods further provide for subject-specific selection of humanized antibody therapies for the treatment of cancer and autoimmune diseases. In some aspects, the humanized antibody includes a first domain that selectively binds to a clonal lineage specific marker protein (CLSMP) on a cell containing the CLSMP and a second domain that selectively binds to an effector antigen on a cell containing the effector antigen. In some cases, the cell containing the effector antigen is the same cell as the cell containing the CLSMP, whereas in other cases, the cell containing the effector antigen and the cell containing the CLSMP are different cells. Optionally, the humanized antibody includes a third domain that selectively binds to a cell surface antigen on the cell containing the CLSMP.

Definitions

The term "a" and "an" can refer to one or to more than one (i.e., to at least one) of the grammatical object of the article. By way of example, "an element" can refer to one element or more than one element.

As used herein, the term "about" can mean plus or minus less than 1 or 1, 2, 3, 4, 5, 6, 7, 8, 9, 10, 11, 12, 13, 14, 15, 16, 17, 18, 19, 20, 25, 30, or greater than 30 percent, depending upon the situation and known or knowable by one skilled in the art.

As used herein, "treat", "treating", or "treatment" refers to any indicia of success in the treatment or amelioration of the disease or condition. For example, "treat", "treating", or "treatment" can refer to reducing, delaying or alleviating the severity of one or more symptoms of the disease or condition, it can include reducing the frequency with which symptoms of a disease, defect, disorder, or adverse condition, and the like, are experienced by a subject, and/or it can include prevention of a disease or condition entirely. As used herein, the term "prevent" or "preventing" can refer to the prevention of the disease or condition, e.g., tumor formation, in a subject. For example, if an subject at risk of developing a tumor or other form of cancer is treated with the methods of the present disclosure and does not later develop the tumor or other form of cancer, then the disease has been prevented, at least over a period of time, in that subject.

As used herein, the term "therapeutically effective" can refer to an amount of a composition or an active component thereof sufficient to provide a beneficial effect or to otherwise reduce a detrimental non-beneficial event to the subject to whom the composition is administered. The term "therapeutically effective" can refer to a dose that produces one or more desired or desirable (e.g., beneficial) effects, wherein the dose can be administered one or more times over a given period of time. The exact dose will depend on the purpose of the treatment, and can be determined by a person having skill in the art using known techniques.

As used herein, a "T Cell Receptor (TCR) fusion protein" or "TFP" can refer to a recombinant polypeptide derived from the various polypeptides comprising the TCR that is generally capable of i) binding to a surface antigen on target cells and ii) interacting with other polypeptide components of the intact TCR complex, typically when co-located in or on the surface of a T cell. As used herein, a "B Cell Receptor (BCR) fusion protein" or "BFP" can refer to a recombinant polypeptide derived from the various polypeptides comprising the BCR that is generally capable of i) binding to a surface antigen on target cells and ii) interacting with other polypeptide components of the intact BCR complex, typically when co-located in or on the surface of a B cell. In some aspects, a TFP or BFP may comprise an antibody binding domain (e.g., a paratope). In some aspects, a TFP or BFP may comprise an antibody. In some aspects, a TFP or BFP may comprise a humanized antibody. In one example, a BFP can comprise one or more polypeptide chains (e.g., a heavy chain and/or light chain) comprising a first domain that selectively binds to a clonal lineage specific marker protein, and a second domain that selectively binds to an effector protein. In another example, a BFP can comprise one or more polypeptide chains (e.g., a heavy chain and/or light chain) comprising a first domain that selectively binds to a clonal lineage specific marker protein, a second domain that selectively binds to an effector protein, and a third domain that selectively binds to a cell surface antigen.

As used herein, the terms "CD5", "CD19", "CD22", "CD23", and "FMC7" may refer genes and/or gene products (e.g., antigenic determinants) detectable on normal B cells, immature B cells, mature B cells, marginal zone B cells, germinal center B cells, memory B cells, B cell leukemia precursor cells, chronic lymphocytic leukemia cells, and/or malignant B cells. The human and murine amino acid and nucleic acid sequences can be found in a public database (e.g., GenBank, UniProt, and/or Swiss-Prot). For example, the amino acid sequence of human CD19 can be found in UniProt/Swiss-Prot Accession No. P15391 and the nucleotide sequence encoding of the human CD19 can be found at Accession No. NM001178098. CD19 is expressed on most B lineage cancers, including, e.g., ALL, CLL and non-Hodgkin's lymphoma (NHL). Other cells that express CD19 are provided below in the definition of "disease associated with expression of CD19." It is also an early marker of normal B cell progenitors. In one example, the antigen-binding portion of TFPs recognizes and binds an epitope within the extracellular domain of the CD19 protein as expressed on a malignant and normal B cell. In some aspects, the present disclosure may comprise a term followed by "+" or "−". A "+" designation may be used to indicate the presence of a compound, gene, and/or gene product (e.g., CD5+ may indicate the presence of the CD5 gene and/or gene product, for example, in the immunophenotype of a chronic lymphocytic leukemia cell). A "−" designation may be used to indicate the absence of a compound, gene, and/or gene product (e.g., CD22− may indicate the absence of the CD22 gene and/or gene product, for example, in the immunophenotype of a chronic lymphocytic leukemia cell).

The term "construct", as used herein, can generally refer to a protein, polypeptide, or polynucleotide comprising one or more binding domains (e.g., a first domain, a second domain, a third domain, an affinity domain, an effector domain, and/or a cell-surface antigen domain). In some instances, two or more binding domains may be coupled by a polynucleotide or polypeptide. In some instances, two or more binding domains may be coupled by electrostatic forces (e.g., covalent or non-covalent binding). In some instances a construct may be a TFP. In some instances, a construct may be a BFP. In some instances, a construct may be an antibody. The term "antibody," as used herein, can refer to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources. The terms "antibody fragment" "antibody binding domain" can refer to at least one portion of an antibody, or recombinant variants thereof, that contains the antigen binding domain or paratope (e.g., an antigenic determining variable region of an intact antibody that is sufficient to confer recognition and specific binding of the antibody fragment to a target, such as an antigen and its defined epitope). Examples of antibody fragments include, but are not limited to, Fab, Fab', F(ab')$_2$, and Fv fragments, single-chain (sc)Fv ("scFv") antibody fragments, linear antibodies, single domain antibodies such as sdAb (either VL or VH), camelid VHH domains, and multi-specific antibodies formed from antibody fragments. The term "scFv" can refer to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. "Heavy chain variable region" or "VH" with regard to an antibody can refer to the fragment of the heavy chain that contains three CDRs interposed between flanking stretches known as framework regions, these framework regions are generally more highly conserved than the CDRs and form a scaffold to support the CDRs. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL. In some instances, a construct or antibody as disclosed herein may be humanized. The term "humanized" may generally be used to describe a polynucleotide or polypeptide whose sequence has been modified to increase its similarity to the sequence of a corresponding polynucleotide or polypeptide in a human. In some instances, a construct or antibody of the present disclosure may comprise two or more binding domains (e.g., a first binding domain, a second domain, a third domain, an affinity domain, an effector domain, and/or a cell-surface antigen domain). A person having skill in the art will appreciate that a binding domain may be specific to a single epitope/antigen, or may bind multiple epitopes/antigens (e.g., a bi-specific binding domain). In some embodiments, two or more domains (e.g., a first domain having an affinity for a first antigen and a second domain having an affinity for a second antigen) may refer to a single binding domain on the construct or antibody having an affinity for both of the first antigen and the second antigen. In some instances, a domain of the present disclosure (e.g., a first binding domain, a second domain, a third domain, an affinity domain, an effector domain, and/or a cell-surface antigen domain) may have an affinity for 1, 2, 3, 4, 5, 6, 7, 8, 9, 10, or more than 10 antigens or epitopes.

The portion of the TFP or BFP comprising an antibody or antibody fragment thereof may exist in a variety of forms where the antigen binding domain is expressed as part of a contiguous polypeptide chain including, for example, a single domain antibody fragment (sdAb), a single chain antibody (scFv) derived from a murine, humanized or human antibody. In one aspect, the antigen binding domain of a TFP or a BFP comprises an antibody fragment. In a further aspect, the TFP or BFP can comprise an antibody fragment that comprises a scFv or a sdAb.

The term "antibody heavy chain," can refer to the larger of the two types of polypeptide chains present in antibody molecules in their naturally occurring conformations, and which normally determines the class to which the antibody belongs. The term "antibody light chain," can refer to the smaller of the two types of polypeptide chains present in antibody molecules in their naturally occurring conformations. Kappa ("κ") and lambda ("λ") light chains can refer to the two major antibody light chain isotypes.

The term "recombinant antibody" can refer to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" can refer to a molecule that is capable of being bound specifically by an antibody, or otherwise provokes an immune response. This immune response may involve either antibody production, or the activation of specific immunologically-competent cells, or both. A person having skill in the art will understand that any macromolecule, such as proteins or peptides, can serve as an antigen. Furthermore, antigens can be derived from recombinant or genomic DNA. A person having skill in the art will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to encode polypeptides that elicit the desired immune response. Moreover, a person having skill in the art will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" can refer to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the present disclosure in prevention of the occurrence of tumor in the first place.

The term "autologous" can refer to any material derived from the same subject to whom it is later to be re-introduced into the subject.

The term "allogeneic" can refer to any material derived from a different animal of the same species or different subject as the subject to whom the material is introduced. Two or more subjects are said to be allogeneic to one another when the genes at one or more loci are not identical. In some aspects, allogeneic material from subjects of the same species may be sufficiently unlike genetically to interact antigenically.

The term "xenogeneic" can refer to a graft derived from an animal of a different species.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin.

"Human" or "fully human" can refer to an immunoglobulin, such as an antibody or antibody fragment, where the whole molecule is of human origin or consists of an amino acid sequence identical to a human form of the antibody or immunoglobulin.

The term "cancer" can refer to a disease characterized by the rapid and uncontrolled growth of aberrant cells. Cancer cells can spread locally or through the bloodstream and lymphatic system to other parts of the body. Examples of various cancers are described herein and include but are not limited to, adrenal cancer, anal cancer, bile duct cancer, bladder cancer, cancer of the blood, bone cancer, a brain tumor, breast cancer, cancer of the cardiovascular system, cervical cancer, colon cancer, cancer of the digestive system, cancer of the endocrine system, endometrial cancer, esophageal cancer, eye cancer, gallbladder cancer, a gastrointestinal tumor, kidney cancer, laryngeal cancer, leukemia, liver cancer, lung cancer, lymphoma, mesothelioma, cancer of the muscular system, Myelodysplastic Syndrome, myeloma, nasal cavity cancer, nasopharyngeal cancer, cancer of the nervous system, cancer of the lymphatic system, oral cancer, oropharyngeal cancer, ovarian cancer, pancreatic cancer, penile cancer, pituitary tumors, prostate cancer, cancer of the reproductive system, cancer of the respiratory system, a sarcoma, salivary gland cancer, skeletal system cancer, skin cancer, small intestine cancer, stomach cancer, testicular cancer, thymus cancer, thyroid cancer, a tumor, cancer of the urinary system, uterine cancer, vaginal cancer, or vulvar cancer. The term 'lymphoma' may refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' may refer to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia.

In some aspects, a disease (e.g., cancer) may be "associated" with expression of CD19. A disease associated with expression of CD19 or condition associated with cells which express CD19 can include, for example, proliferative diseases such as a cancer or malignancy or a precancerous condition such as a myelodysplasia, a myelodysplastic syndrome or a pre-leukemia; or a non-cancer related indication associated with cells which express CD19. In one aspect, a cancer associated with expression of CD19 is a hematological cancer. In one aspect, the hematological cancer is a leukemia or a lymphoma. In one aspect, a cancer associated with expression of CD19 includes cancers and malignancies including, but not limited to, e.g., one or more acute leukemias including but not limited to, e.g., B cell ALL, T-cell acute lymphoid leukemia (TALL), one or more chronic leukemias including but not limited to, e.g., CLL or chronic myelogenous leukemia (CML). Additional cancers or hematologic conditions associated with expression of CD19 comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "pre-leukemia" which are a diverse collection of hematological conditions united by ineffective production (or dysplasia) of myeloid blood cells, and the like. Further diseases associated with expression of CD19 expression include, but are not limited to, e.g., atypical and/or non-classical cancers, malignancies, precancerous conditions or proliferative diseases associated with expression of CD19. Non-cancer related indications associated with expression of CD19 include, but are not limited to, e.g., autoimmune disease, (e.g., lupus, rheumatoid arthritis, colitis), inflammatory disorders (allergy and asthma), and transplantation.

The term "stimulation," can refer to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

The term "stimulatory molecule" or "stimulatory domain" can refer to a molecule or portion thereof expressed by a cell (e.g., a B cell or a T cell) that provides the primary cytoplasmic signaling sequence(s) that regulate primary activation of the receptor complex (e.g., a BCR or TCR) in a stimulatory way for at least some aspect of the cell signaling pathway. In one example, a primary signal can be initiated by binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or "ITAM". Examples of an ITAM containing primary cytoplasmic signaling sequence can include those derived from TCR zeta, FcR gamma, FcR beta, CD3 gamma, CD3 delta, CD3 epsilon, CD5, CD22, CD79a, CD79b, CD278 (also known as "ICOS") and CD66d.

The term "antigen presenting cell" or "APC" can refer to an immune system cell such as an accessory cell (e.g., a B-cell, a dendritic cell, and the like) that displays a foreign antigen complexed with major histocompatibility complexes (MHC's) on its surface. B-cells may recognize these complexes using their B-cell receptors (BCRs). T-cells may recognize these complexes using their T-cell receptors (TCRs).

The term "costimulatory molecule" can refer to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137). A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like. The intracellular signaling domain can comprise the entire intracellular portion, or the entire native intracellular signaling domain, of the molecule from which it is derived, or a functional fragment thereof. The term "4-1BB" can refer to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc No. AAA62478.2, or the equivalent residues from a non-human species (e.g., mouse, rodent, monkey, ape and the like).

The term "encoding" can refer to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain one or more introns.

The term "endogenous" can refer to any material from or produced inside an organism, cell, tissue or system.

The term "exogenous" can refer to any material introduced from or produced outside an organism, cell, tissue or system.

The term "expression" can refer to the transcription and/or translation of a particular nucleotide sequence driven by a promoter.

The term "transfer vector" can refer to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" can refer to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" can refer to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" can refer to a vector derived from at least a portion of a lentivirus genome, including a self-inactivating lentiviral vector. Other non-limiting examples of lentivirus vectors that may be used in the clinic include the LENTIVECTOR® gene delivery technology (Oxford BioMedica), the LENTIMAX™ vector system (Lentigen), and the like. Nonclinical types of lentiviral vectors are also available and would be known to one skilled in the art.

The term "homologous" or "identity" can refer to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences corresponds to the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present disclosure, the following abbreviations for the commonly occurring nucleic acid bases are used. "A" can refer to adenosine, "C" can refer to cytosine, "G" can refer to guanosine, "T" can refer to thymidine, and "U" can refer to uridine.

The term "operably linked" or "transcriptional control" can refer to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "nucleic acid" or "polynucleotide" can refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term can refer to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" can refer to a DNA sequence recognized by the transcription machinery of the cell, or introduced synthetic machinery, required to initiate the specific transcription of a polynucleotide sequence.

The term "promoter/regulatory sequence" can refer to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter can refer to a nucleotide sequence which, when operably linked with a polynucleotide which encodes or specifies a gene product, causes the gene product to be produced in a cell under most or all physiological conditions of the cell.

The term "inducible" promoter can refer to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter can refer to a nucleotide sequence which, when operably linked with a polynucleotide encodes or specified by a gene, causes the gene product to be produced in a cell substantially only if the cell is a cell of the tissue type corresponding to the promoter.

The terms "linker" and "flexible polypeptide linker" as used in the context of a scFv can refer to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$, where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, $(Gly_4 Ser)_4$ or $(Gly_4Ser)_3$. In another embodiment, the linkers include multiple repeats of $(Gly_2Ser)$, $(GlySer)$ or $(Gly_3Ser)$. Also included within the scope of the present disclosure are linkers described in WO2012/138475.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" can refer to RNA, preferably mRNA, which has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. Poly(A) sequences can be modified chemically or enzymatically to modulate mRNA functionality such as localization, stability or efficiency of translation.

As used herein, "polyadenylation" can refer to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly (A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" can refer to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" can refer to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term, a "substantially purified" cell can refer to a cell that is essentially free of other cell types. A substantially purified cell also can refer to a cell which has been separated from other cell types with which it is normally associated in its naturally occurring state. In some instances, a population of substantially purified cells can refer to a homogenous population of cells. In other instances, this term can refer simply to cell that have been separated from the cells with which they are naturally associated in their natural state. In some aspects, the cells are cultured in vitro. In other aspects, the cells are not cultured in vitro.

Antibody Diversity, Idiotype Immunoglobulins, B-Cell Diversity and B-Cell Malignancies The broad antibody repertoire generated by B-lymphocytes (B-cells) in humans arises from the rearrangement and hypermutation of one each from a cluster of multiple, distinct immunoglobulin heavy (IgH) and light genes. In every mature immunoglobulin, one gene each from amongst the variable (V), diversity (D) and joining (J) gene families are randomly combined, trimmed, and subsequently hypermutated to ensure a highly-random complementarity-determining region (CDR). CDR3 is therefore the most diverse segment of the IgH variable domain.

Idiotype Immunoglobulins in B-Cell Chronic Lymphocytic Leukemia

Chronic lymphocytic leukemia (B-CLL; CLL) is a human malignancy characterized by a rapidly advancing accumulation of monoclonal B-lymphocytes, and harbors a characteristic immunophenotype. Usually presenting as CD5+ CD23+CD19+CD22−FMC7+, these cells also usually overexpress the anti-apoptotic Bcl-2 marker and surface immunoglobulins (sIg; Ig; Id). These surface immunoglobulins (clonally-specific and referred to as idiotype proteins), are clonal in nature and in surface expression are usually of IgD and IgM isotype.

The CDR3 of the V-domain of the IgH heavy chain (VH) plays a central role in immunoglobulin binding diversity. Due to the accumulated effects of VDJ recombination and somatic hypermutation processes inherent in B-cell development, the normal chances for two independent (normal) B-cell clones to carry identical VH CDR3 are almost negligible.

As in normal B-cells, recombined IGHV genes in B-CLL undergo somatic hypermutation, with the degree of divergence from germline IGHV genes broadly defining two distinct subtypes of the disease with differing clinical courses: mutated IGHV (<98% homology to germline IGHV genes) follow an indolent course, and unmutated IGHV CLL following a more aggressive course.

A humanized antibody can be produced using a variety of techniques known in the art, including but not limited to, CDR-grafting, veneering or resurfacing, and chain shuffling. Framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions.

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can be performed, for example, by substituting rodent CDRs or CDR sequences for the corresponding sequences of a human antibody (e.g., CDR-grafting). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing or chain shuffling.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies. In some embodiments, the framework region, e.g., all four framework regions, of the heavy chain variable region are derived from a VH4-4-59 germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a VK3-1.25 germline sequence. In one embodiment, the framework region can comprise, one, two, three, four or five modifications, e.g., substitutions, e.g., from the amino acid at the corresponding murine sequence.

In some aspects, the portion of a BFP or TFP that comprises an antibody or fragment thereof is humanized with retention of high affinity for the target antigen and other favorable biological properties. According to one aspect of the present disclosure, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

IGHV* Targeted Monoclonal Antibodies

Figure 3:
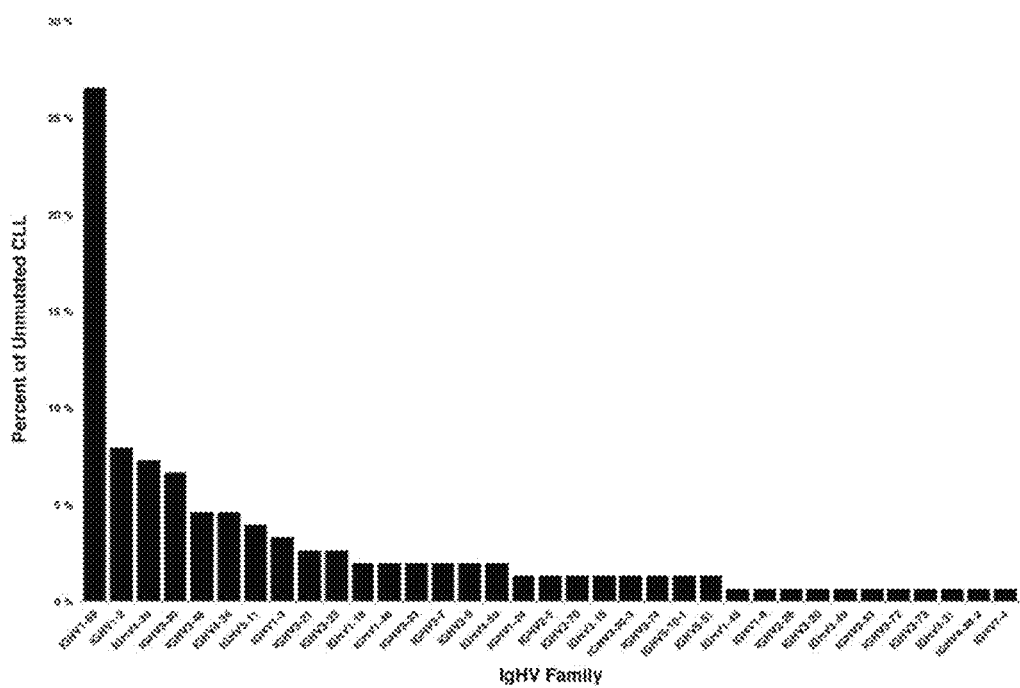
FIG. 3 depicts the most prevalent IGHV classes in unmutated chronic lymphocytic leukemia (CLL).
Figure 4:
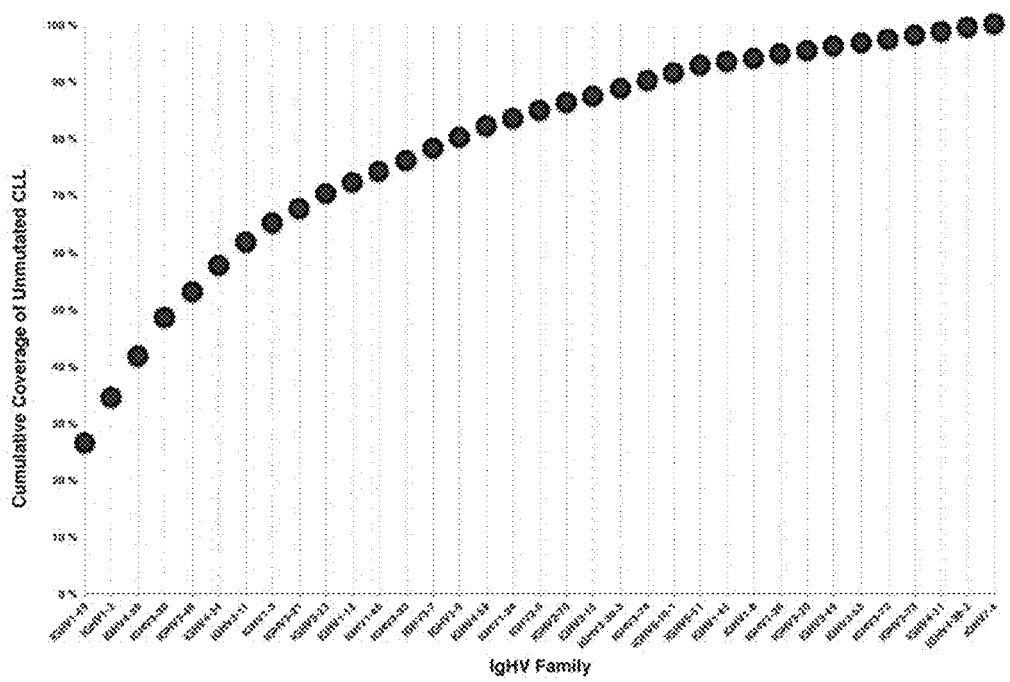
FIG. 4 depicts IGHV class coverage in unmutated chronic lymphocytic leukemia (CLL).
Figure 5:
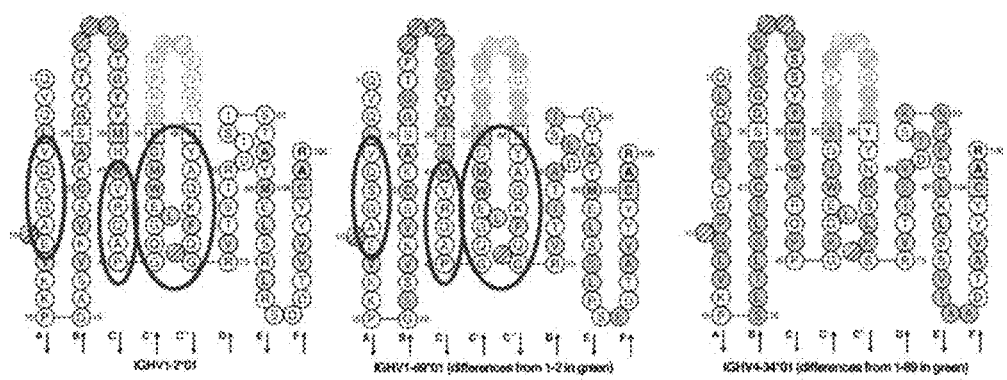
FIG. 5 depicts conserved structural "motifs" across IGHV genes that can be suitable targets for the compositions and methods disclosed herein.
Figure 6:
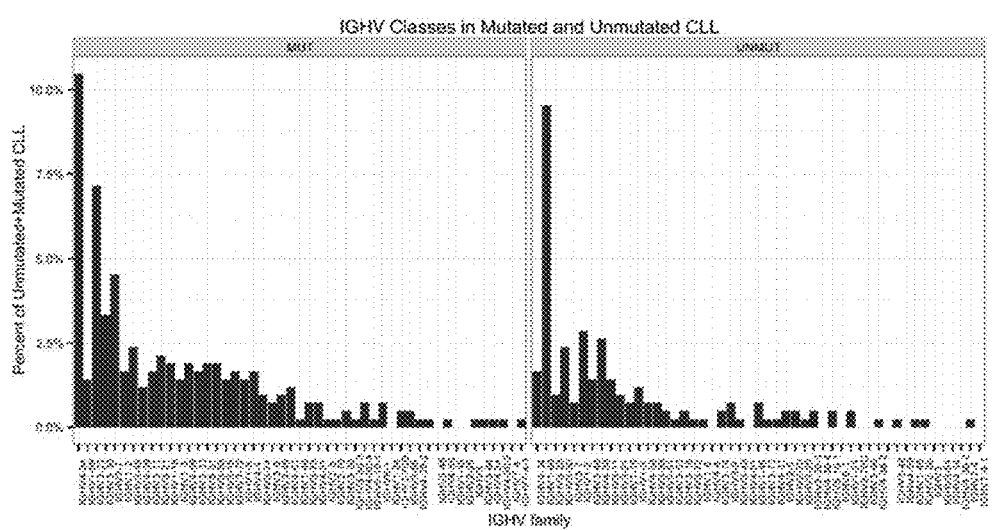
FIG. 6 depicts a comparison of IGHV classes between mutated and unmutated chronic lymphocytic leukemia (CLL).

The IGHV1-69 gene is expressed by approximately 20-30% of unmutated CLL cases with other IGHV* gene as shown in FIG. 3. Genes representing other IGHVs prevalent in unmutated CLL cases can (percent of the unmutated IGHV) include: IGHV1-2 (9.22%), IGHV3-30 (4.26%), IGHV3-48 (4.96%), etc. In one aspect of the present disclosure, a panel of specific humanized monoclonal antibodies (with and/or without bi-specific or tri-specific mAb domains) against these variants can be manufactured, and subsequently, a biological sample from a subject can be sequenced in order to determine which of the antibodies amongst the pre-manufactured antibody panel could be selected for administration to the subject. A similar approach may be used to treat acute myeloid leukemia (AML) or acute lymphocytic leukemia (ALL).

Non-limiting examples of IGHV genes that can be targeted with a humanized antibody of the disclosure can include: IGHV1-18*01, IGHV1-18*02, IGHV1-18*03, IGHV1-2*01, IGHV1-2*02, IGHV1-2*03, IGHV1-2*04, IGHV1-2*05, IGHV1-24*01, IGHV1-3*01, IGHV1-3*02, IGHV1-45*01, IGHV1-45*02, IGHV1-45*03, IGHV1-46*01, IGHV1-46*02, IGHV1-46*03, IGHV1-58*01, IGHV1-58*02, IGHV1-69*01, IGHV1-69*02, IGHV1-69*03, IGHV1-69*04, IGHV1-69*05, IGHV1-69*06, IGHV1-69*07, IGHV1-69*08, IGHV1-69*09, IGHV1-69*10, IGHV1-69*11, IGHV1-69*12, IGHV1-69*13, IGHV1-8*01, IGHV1-8*02, IGHV1-c*01, IGHV1-f*01, IGHV1-f*02, IGHV1/OR15-1*01, IGHV1/OR15-1*02, IGHV1/OR15-1*03, IGHV1/OR15-1*04, IGHV1/OR15-5*01, IGHV1/OR15-5*02, IGHV1/OR15-9*01, IGHV1/OR21-1*01, IGHV2-26*01, IGHV2-5*01, IGHV2-5*02, IGHV2-5*03, IGHV2-5*04, IGHV2-5*05, IGHV2-5*06, IGHV2-5*07, IGHV2-5*08, IGHV2-5*09, IGHV2-5*10, IGHV2-70*01, IGHV2-70*02, IGHV2-70*03, IGHV2-70*04, IGHV2-70*05, IGHV2-70*06, IGHV2-70*07, IGHV2-70*08, IGHV2-70*09, IGHV2-70*10, IGHV2-70*11, IGHV2-70*12, IGHV2-70*13, IGHV2/OR16-5*01, IGHV3-11*01, IGHV3-11*03, IGHV3-11*04, IGHV3-11*05, IGHV3-13*01, IGHV3-13*02, IGHV3-13*03, IGHV3-13*04, IGHV3-15*01, IGHV3-15*02, IGHV3-15*03, IGHV3-15*04, IGHV3-15*05, IGHV3-15*06, IGHV3-15*07, IGHV3-15*08, IGHV3-16*01, IGHV3-16*02, IGHV3-20*01, IGHV3-21*01, IGHV3-21*02, IGHV3-21*03, IGHV3-21*04, IGHV3-23*01, IGHV3-23*02, IGHV3-23*03, IGHV3-23*04, IGHV3-23*05, IGHV3-25*04, IGHV3-30*01, IGHV3-30*02, IGHV3-30*03, IGHV3-30*04, IGHV3-30*05, IGHV3-30*06, IGHV3-30*07, IGHV3-30*08, IGHV3-30*09, IGHV3-30*10, IGHV3-30*11, IGHV3-30*12, IGHV3-30*13, IGHV3-30*14, IGHV3-30*15, IGHV3-30*16, IGHV3-30*17, IGHV3-30*18, IGHV3-30*19, IGHV3-30-3*01, IGHV3-30-3*02, IGHV3-33*01, IGHV3-33*02, IGHV3-33*03, IGHV3-33*04, IGHV3-33*05, IGHV3-33*06, IGHV3-35*01, IGHV3-38*01, IGHV3-38*02, IGHV3-43*01, IGHV3-43*02, IGHV3-48*01, IGHV3-48*02, IGHV3-48*03, IGHV3-48*04, IGHV3-49*01, IGHV3-49*02, IGHV3-49*03, IGHV3-49*04, IGHV3-49*05, IGHV3-53*01, IGHV3-53*02, IGHV3-53*03, IGHV3-53*04, IGHV3-64*01, IGHV3-64*02, IGHV3-64*03, IGHV3-64*04, IGHV3-64*05, IGHV3-66*01, IGHV3-66*02, IGHV3-66*03, IGHV3-66*04, IGHV3-7*01, IGHV3-7*02, IGHV3-7*03, IGHV3-72*01, IGHV3-72*02, IGHV3-73*01, IGHV3-73*02, IGHV3-74*01, IGHV3-74*02, IGHV3-74*03, IGHV3-9*01, IGHV3-9*02, IGHV3-NL1*01, IGHV3-d*01, IGHV3/OR15-7*01, IGHV3/OR15-7*02, IGHV3/OR15-7*03, IGHV3/OR15-7*05, IGHV3/OR16-10*01, IGHV3/OR16-10*02, IGHV3/OR16-10*03, IGHV3/OR16-12*01, IGHV3/OR16-13*01, IGHV3/OR16-6*02, IGHV3/OR16-8*01, IGHV3/OR16-8*02, IGHV3/OR16-9*01, IGHV4-28*01, IGHV4-28*02, IGHV4-28*03, IGHV4-28*04, IGHV4-28*05, IGHV4-28*06, IGHV4-30-2*01, IGHV4-30-2*02, IGHV4-30-2*03, IGHV4-30-2*04, IGHV4-30-2*05, IGHV4-30-4*01, IGHV4-30-4*02, IGHV4-30-4*03, IGHV4-30-4*04, IGHV4-30-4*05, IGHV4-30-4*06, IGHV4-31*01, IGHV4-31*02, IGHV4-31*03, IGHV4-31*04, IGHV4-31*05, IGHV4-31*06, IGHV4-31*07, IGHV4-31*08, IGHV4-31*09, IGHV4-31*10, IGHV4-34*01, IGHV4-34*02, IGHV4-34*03, IGHV4-34*04, IGHV4-34*05, IGHV4-34*06, IGHV4-34*07, IGHV4-34*08, IGHV4-34*09, IGHV4-34*10, IGHV4-34*11, IGHV4-34*12, IGHV4-34*13, IGHV4-39*01, IGHV4-39*02, IGHV4-39*03, IGHV4-39*04, IGHV4-39*05, IGHV4-39*06, IGHV4-39*07, IGHV4-4*01, IGHV4-4*02, IGHV4-4*03, IGHV4-4*04, IGHV4-4*05, IGHV4-4*06, IGHV4-4*07, IGHV4-59*01, IGHV4-59*02, IGHV4-59*03, IGHV4-59*04, IGHV4-59*05, IGHV4-59*06, IGHV4-59*07, IGHV4-59*08, IGHV4-59*09, IGHV4-59*10, IGHV4-61*01, IGHV4-61*02, IGHV4-61*03, IGHV4-61*04, IGHV4-61*05, IGHV4-61*06, IGHV4-61*07, IGHV4-61*08, IGHV4-b*01, IGHV4-b*02, IGHV4/OR15-8*01, IGHV4/OR15-8*02, IGHV4/OR15-8*03, IGHV5-51*01, IGHV5-51*02, IGHV5-51*03, IGHV5-51*04, IGHV5-51*05, IGHV5-a*01, IGHV5-a*03, IGHV5-a*04, IGHV6-1*01, IGHV6-1*02, IGHV7-4-1*01, IGHV7-4-1*02, IGHV7-4-1*03, IGHV7-4-1*04, IGHV7-4-1*05, or IGHV7-81*01, IGHV1-69, IGHV1-2, IGHV4-39, IGHV3-30, IGHV3-48, IGHV4-34, IGHV3-11, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV1-45, IGHV1-8, IGHV2-26, IGHV3-20, IGHV3-49, IGHV3-53, IGHV3-72, IGHV3-73, IGHV4-31, IGHV4-38-2, and IGHV7-4.

Also provided herein are methods for obtaining an antibody antigen binding domain specific for a target antigen (e.g., CD19 or any target antigen described elsewhere herein for targets of fusion moiety binding domains), the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for a target antigen of interest (e.g., CD19) and optionally with one or more desired properties.

In some instances, VH domains and scFvs can be prepared according to method known in the art. scFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intra-chain folding is prevented. Inter-chain folding is also required to bring the two variable regions together to form a functional epitope binding site.

An scFv can comprise a linker of about 10, 11, 12, 13, 14, 15 or greater than 15 residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_n$, where n is a positive integer equal to or greater than 1. In one embodiment, the linker can be $(Gly_4Ser)_4$ or $(Gly_4Ser)_3$. Variation in the linker length may retain or enhance activity, giving rise to superior efficacy in activity studies.

Mutations

In one aspect, the antigen binding domain of the BFP or TFP comprises an amino acid sequence that is homologous to an antigen binding domain amino acid sequence described herein. In one specific aspect, the BFP or TFP comprises an antibody fragment. In a further aspect, that antibody fragment comprises an scFv.

In various aspects, the antigen binding domain of the BFP or TFP is engineered by modifying one or more amino acids within one or both variable regions (e.g., VH and/or VL), for example within one or more CDR regions and/or within one or more framework regions. In one specific aspect, the BFP or TFP composition of the present disclosure comprises an antibody fragment. In a further aspect, that antibody fragment comprises an scFv.

It will be understood by one of ordinary skill in the art that the antibody or antibody fragment of the present disclosure may further be modified such that they vary in amino acid sequence (e.g., from wild-type), but not in desired activity. For example, additional nucleotide substitutions leading to amino acid substitutions at "non-essential" amino acid residues may be made to the protein. For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, can refer to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, for example, by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology). Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

In one aspect, the present disclosure contemplates modifications of the starting antibody or fragment (e.g., scFv) amino acid sequence that generate functionally equivalent molecules. For example, the VH or VL of an anti-CD19 binding domain, e.g., scFv, comprised in the BFP or TFP can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-CD19 binding domain, e.g., scFv. The present disclosure contemplates modifications of the entire BFP or TFP construct, e.g., modifications in one or more amino acid sequences of the various domains of the TFP construct in order to generate functionally equivalent molecules. The BFP or TFP construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting BFP or TFP construct.

Anti-Id X Surface Lineage Marker Bi-Specific Antibodies

Affinity library screening often yields a large diversity of affinity reagents, but these may in vivo possess less than optimal binding/affinity to their intended targets. Modern bi-specific antibodies can combine two antigen-binding sites with distinct specificities in one single protein molecule. In some cases, the humanized antibody of the disclosure is a bi-specific antibody with two antigen-binding domains.

Bi-Specific T-Cell Engagers

A BiTE (bi-specific T-cell engager; blinatu-momab; a single-chain (sc) Fv-based CD19Xcd3 targeting molecule) is capable of bispecific binding to CD3- and CD19-positive cells, able to redirect both pre-stimulated and unstimulated human T cells for lysis of human B lymphoma cells (e.g., cell lines). Overall, the molecule can have 700- and 8000-fold higher efficacy than a comparable tandem diabody molecules in effecting T-cell lysis of tumor.

In some aspects, the pairing of an idiotype-specific molecule with a CD3 domain to effect similar outcomes against IGHV* and Id-bearing lymphoma cells is envisioned.

IGH* Repertoire Profiling by Next-Gen Sequencing

A number of approaches exist, including some commercially-available tests (by Sequenta, Inc. and Adaptive Biotechnologies, Inc.), which allow for massively parallel sequencing of IGH genes in subject tissue samples (blood, tumor, etc.). These approaches allow broad profiling of B-lymphocyte populations in a subject, and are useful for clonality monitoring of diagnosed tumors, as well as for post-therapy follow-up of tumor progression. These tests, relying on individually-separated PCR amplification and massively parallel sequencing of single IGH genes, are performed on next-generation sequencing instruments (Illumina, Roche 454, Ion PGM/Torrent), and can profile a representative subset of IGH genes corresponding to individual B-lymphocytes in a tumor or blood sample. Specifically, consensus IGH-specific primers exist (e.g., from the BIOMED-2 consortium) which facilitate amplification subsequent sequencing of individual IGHV/D/J genes from a sample. Following amplification and sequencing, individual sequence sets can be quality-controlled, clustered by similarity, and gene-aligned to reference (e.g. germline human) IgHV/D/J genes. In some implementations, the BIOMED-2 primers have been used to amplify IGH sequences for diagnostic use to identify mutational status in CLL subjects. Others have used the BIOMED-2 primers to amplify and massively parallel sequence a number of hematologic malignancies for clonality.

In some aspects of the present disclosure, a biological sample from an unmutated CLL subject is sequenced in order to determine IGHV* usage, such that the most suitable anti-IGHV antibody for that subject's disease can be selected. For example, a subject with diagnosed CLL could provide a tumor sample (perhaps the sample obtained during initial tumor staging, or a new sample, or a blood sample), and from that sample, an IGHV clonality sequence profile (e.g. the IGHV sequence most commonly found in the sample) can be determined, as well as the mutational status of the IGHV gene (e.g., >98% identity to the reference germline IGHV according to IgBlast). In one example, if the subject were suffering from a lymphoma with predominantly IGHV1-69+ lymphocytes, and the IGHV1-69 sequence were determined to be >98% identical to the germline reference IGHV1-69, then it could be recommended to treat the subject with an anti-IGHV1-69 antibody of the disclosure.

Clonal Lineage Specific Marker Proteins (CLSMPs)

The humanized antibodies described herein can be suitable for the treatment of a subject in need thereof by targeting the humanized antibody to a clonal lineage specific marker protein (CLSMPs) on a clonal population of cells. As used herein, the term "clonal lineage specific marker proteins" or CLSMPs may generally refer to genetically encoded proteins expressed uniquely in cells of a specific clonal cell lineage.

In a non-limiting example, a CLSMP can be the idiotype defining the antibody uniquely expressed by a clonal B cell population. B cell idiotypes, also known as B cell receptors (BCR), are comprised of two protein chains: a heavy chain and a light chain. The heavy chain is encoded by a gene created through somatic cell recombination of an IGHV segment with D, J and C genes through VDJC recombination. The light chain is encoded by a gene created through somatic cell recombination of an IGLV gene with J and C regions through VJC recombination. IGLV genes include both lambda and kappa IGLV genes. Each clonal population of B cells expresses a unique idiotype. They are encoded by the B cell genome, they are unique to B cells of this lineage, and they are expressed on the cell surface.

Another non-limiting example of a CLSMP is the T cell receptor (TCR) expressed on the surface of a clonal lineage of T cells. TCRs are comprised of two chains: alpha and beta chains or gamma and delta chains. The TCR alpha or gamma chain is encoded by a gene created through somatic cell recombination of V and J genes. The TCR beta or delta chain is encoded by a gene created through recombination of V, D and J genes. Each clonal population of T cells expresses a unique TCR. TCRs are encoded by the T cell genome, they are unique to T cells of this lineage, and they are expressed on the cell surface.

Cancers undergo somatic mutations, and cancer genomes differ from normal tissues in having many, often thousands, of point mutations, insertions, deletions and genomic rearrangements. These mutations or genomic aberrations become markers of the tumor lineage. When these non-synonymous point mutations or genomic aberrations involve protein coding genes, they generate CLSMP. Thus, non-synonymous point mutations or genomic aberrations involving protein coding genes are another example of CLSMPs. The collection of aberrant proteins expressed by tumors as a result of mutations in the cancer genome (termed "tumor neoantigens") is often referred to as the cancer mutanome. In some cases, the CLSMP is a tumor neoantigen or a lineage-specific protein alteration. In some instances, a tumor neoantigen can comprise a neoepitope (e.g., a neoantigen specific epitope). In some instances, an antibody or construct of the present disclosure can be an anti-neoantigen agent. In some instances, an antibody or construct of the present disclosure can be an anti-neoepitope agent.

Another non-limiting example of CLSMP can include novel or aberrant proteins expressed by cancer cells through somatic recombination or translocation. For example, the Philadelphia Chromosome (PC) has long been used as a marker of cancerous cell in chronic myelogenous leukemia (CML) lineage. The PC is formed through a reciprocal translocation between chromosome 9 and chromosome 22, which is specifically designated t(9;22)(q34;q11) fusing the BCR and ABL genes. The BCR-ABL fusion protein can be a CLSMP.

Yet another non-limiting example of CLSMPs can include proteins synthesized through aberrant splicing of proteins in a tumor that are not expressed in normal cells. In another example, genetic events in cancers can lead to the inactivation or deletion of genes required for normal transcription and splicing of transcripts. These events are lineage specific markers of the cancer cells. As a result of the inactivation or deletion of a gene required for normal transcript processing, many cancers exhibit extensive patterns of aberrant transcription and aberrant splicing that lead to the production of aberrant protein products. Because these aberrant protein products are a consequence lineage specific event, these aberrant proteins can be CLSMPs. In another example, genetic events in cancers can lead to the inactivation or deletion of genes required for the normal processing of proteins. These events are lineage specific markers of the cancer cells. As a result of the inactivation or deletion of genes required for normal protein processing, many cancers express proteins with aberrant glycosylation, aberrant phosphorylation or other aberrant post translational modifications. These aberrantly processed proteins are CLSMP. In another example, genetic events in cancers can lead to the inactivation or deletion of genes required for the normal transport and localization of proteins. These events are lineage specific markers of the cancer cells. As a result of the inactivation or deletion of gene required for normal protein transport and localization, many cancers express proteins with aberrant localization. For example, proteins normally present only in the nucleus, specific organelles or the cytoplasm may be aberrantly expressed on the cell surface of cancer cells. These aberrantly localized proteins can be CLSMPs.

Cell Surface Antigens

The humanized antibodies described herein can contain a domain that selectively binds to a cell surface antigen on a cell. In some cases, the cell is a CLSMP-expressing cell. In one non-limiting example, CD20 can be a cell surface antigen targeted by a humanized antibody. CD20 is expressed on all B lymphocytes. B lymphocytes as a cell type are not a clonal population but rather a group of cells derived from multiple independent progenitors through a common differentiation pathway. Therefore, CD20 is a B cell type specific marker. Similarly CD14 is expressed by macrophages, dendritic cells and at a lower level by neutrophils. CD14 positive cells are derived from a common set of myeloid progenitors, and therefore, CD14 can be a cell surface antigen. Another example of a cell surface antigen is HER2/neu. HER2/neu is normally expressed on the surface of epithelial cells in the gastrointestinal, respiratory, reproductive, and urinary tract as well as in the skin, breast and placenta. Because HER2/neu is expressed in multiple other tissues, it is not specific to any specific cell lineage.

Effector Antigens

The humanized antibodies disclosed herein include protein-binding domains that selectively bind to an effector antigen. In some cases, the effector antigen is presented on the surface of a cell. The cell containing the effector antigen can be the same cell as the cell containing the CLSMP or can be a different cell. Non-limiting examples of effector antigens suitable for use with the compositions and methods herein include: CD3, CD28, CTLA4, PD-1, or IL-2R. In some cases, the effector antigen is a toxin such as *Pseudomonas* exotoxin or diphtheria toxin. In some cases, the effector antigen can comprise an Fc receptor. An Fc receptor may generally refer to a protein found on the surface of some cells B lymphocytes, follicular dendritic cells, natural killer cells, macrophages, neutrophils, eosinophils, basophils, human platelets, and mast cells) that contribute to the protective functions of the immune system. Fc receptors may bind to antibodies that are attached to infected cells or invading pathogens. Their activity stimulates phagocytic or cytotoxic cells to destroy microbes, or infected cells by antibody-mediated phagocytosis or antibody-dependent cell-mediated cytotoxicity. For example, an embodiment of the present disclosure can comprise a first domain having an affinity for a CLSMP found on a tumor cell and a second domain having an affinity for an Fc receptor found on an effector cell (e.g., B lymphocytes, follicular dendritic cells, natural killer cells, macrophages, neutrophils, eosinophils, basophils, human platelets, or mast cells). There are several different types of Fc receptors, which can be classified based on the type of antibody that they recognize. Non-limiting examples of Fc receptors include Fc-gamma receptors, Fc-alpha receptors, Fc-epsilon receptors, FcγRI (e.g., CD64), FcγRIIA (e.g., CD32), FcγRIIB1 (e.g., CD32), FcγRIIB2 (e.g., CD32), FcγRIIIA (e.g., CD16a), FcγRIIIB (e.g., CD16b), FcεRI, FcεRII (e.g., CD23), FcαRI (e.g., CD89), Fcα/μR, and FcRn.

In some aspects, a humanized antibody selectively binds to an effector antigen on a T-cell to target the T-cell to a malignant or aberrant cell. For example, the antibody may selectively bind to CD3 on a T lymphocyte and selectively bind to a CLSMP on a cancer cell. When administered to a subject, the T lymphocyte may be activated and kill the cancer cell expressing the CLSMP.

Indications

The compositions and methods described herein can be used to treat cancer and autoimmune diseases. In some cases, the cancer is a B cell malignancy. B cell malignancies include chronic lymphocytic leukemia (CLL), mantle cell lymphoma (MCL), follicular lymphoma (FL). These diseases are characterized by an indolent but relentless course. CLL, MCL and FL are caused by the aberrant clonal proliferation of B lymphocyte or B lymphocyte progenitors. Cells of these cancers express a B cell receptor (BCR) with an idiotype that is unique to the tumor lineage. Tumor cells can readily be obtained through biopsy, or in the case of CLL a blood sample. The sequence of the idiotype, including assessment of microheterogeneity, can be assessed through selective sequence amplification followed by molecular sequence analysis. PCR cloned idiotype genes from a cancer can be used to develop an anti-idiotype therapeutic as described herein. The therapeutic can be administered intravenously. When administered, the therapeutic can induce immune cells to attack and kill the cancer cells.

Other non-limiting examples of cancers that can be treated by the compositions and methods herein include: B-cell lymphoma including Small Lymphocytic Lymphoma, Marginal Zone Lymphomas, Gastric MALT Lymphoma, Nongastric MALT Lymphoma, Nodal Marginal Zone Lymphoma, Splenic Marginal Zone Lymphoma, Diffuse Large B-Cell Lymphoma, Burkitt's Lymphoma, Lymphoblastic Lymphoma, AIDS-Related B-Cell Lymphomas, Hairy Cell Leukemia, Primary Cutaneous B-Cell Lymphomas, Waldenström's Macroglobulinemia/Lymphoplasmacytic Lymphoma; T cell lymphomas including: Peripheral T-Cell Lymphomas, Mycosis Fungoides/Sezary Syndrome, Primary Cutaneous CD30+ T-Cell, Lymphoproliferative Disorders, T-cell Large Granular Lymphocytic Leukemia, Adult T-Cell Leukemia/Lymphoma, T-Cell Prolymphocytic Leukemia, Extranodal NK/T-Cell Lymphoma, Post-Transplant Lymphoproliferative Disorders, Castleman's Disease; Leukemias including: Acute Lymphoblastic Leukemia, Acute Myeloid Leukemia, Chronic Myelogenous Leukemia, Myelodysplastic Syndromes, and any other disease, dysplasia, or malignancy disclosed herein.

In some cases, the compositions and methods described herein can be used to treat autoimmune diseases, including rheumatoid arthritis, Sjögren's syndrome and type I diabetes. In some cases, the disease is an autoimmune-like disease such as graft versus host disease. Autoimmune diseases including rheumatoid arthritis and Sjögren's syndrome are characterized by the presence of abnormal anti-self antibodies. In many subjects, these autoantibodies are produced by a single abnormal clonal lineage of B lymphocytes. These abnormal B lymphocytes are enriched at sites of inflammation such as inflamed joints, and these cells can readily be obtained by joint aspiration. The B lymphocytes producing the abnormal antibody also express that antibody on their cell surface. The sequence of the idiotype, including assessment of microheterogeneity, can be assessed through selective sequence amplification followed by molecular sequence analysis. PCR cloned idiotype genes from a cancer can be used to develop an anti-idiotype therapeutic as described herein. The therapeutic can be administered intravenously. When administered, the therapeutic will induce immune cells to attack and kill the clonal lineage of B lymphocytes producing the abnormal anti self antibody to prevent the development or progression of arthritis.

Subjects

In some embodiments, the methods and compositions disclosed herein can be used in the treatment of cancer a subject. The subject may be any human subject, particularly a cancer patient, a subject at risk for cancer, or a subject with a family or personal history of cancer. In some cases, the subject is in a particular stage of cancer treatment. In some cases, the subject may be administered a composition of the present disclosure concurrently with another treatment (e.g., radiation therapy).

The subject may have any type of cancer. Examples of cancer can include, but are not limited to, adrenal cancer, anal cancer, bile duct cancer, bladder cancer, cancer of the blood, bone cancer, a brain tumor, breast cancer, cancer of the cardiovascular system, cervical cancer, colon cancer, cancer of the digestive system, cancer of the endocrine system, endometrial cancer, esophageal cancer, eye cancer, gallbladder cancer, a gastrointestinal tumor, kidney cancer, laryngeal cancer, leukemia, liver cancer, lung cancer, lymphoma, mesothelioma, cancer of the muscular system, Myelodysplastic Syndrome, myeloma, nasal cavity cancer, nasopharyngeal cancer, cancer of the nervous system, cancer of the lymphatic system, oral cancer, oropharyngeal cancer, ovarian cancer, pancreatic cancer, penile cancer, pituitary tumors, prostate cancer, cancer of the reproductive system, cancer of the respiratory system, a sarcoma, salivary gland cancer, skeletal system cancer, skin cancer, small intestine cancer, stomach cancer, testicular cancer, thymus cancer, thyroid cancer, a tumor, cancer of the urinary system, uterine cancer, vaginal cancer, or vulvar cancer. The term 'lymphoma' may refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' may refer to any type of leukemia including acute leukemia or chronic leukemia. Types of leukemia can include acute myeloid leukemia, chronic myeloid leukemia, acute lymphocytic leukemia, acute undifferentiated leukemia, or chronic lymphocytic leukemia.

A subject treated by any of the methods or compositions described herein may be of any age and may be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). Furthermore, a patient treated by any of the methods or compositions described herein may be male or female.

Any of the compositions disclosed herein may also be administered to a non-human subject, such as a laboratory or farm animal. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

Samples

Samples to be used in the methods described herein can include any biological material which may contain nucleic acid. Samples may originate from a variety of sources. In some embodiments, the sources may be, for example, humans, non-human mammals, mammals, animals, rodents, amphibians, fish, reptiles, microbes, bacteria, plants, fungus, yeast and/or viruses. In some embodiments, the sample may be a biological sample. In some embodiments, the biological sample may include, for example, cell cultures, tissue sections, frozen sections, biopsy samples and autopsy samples. The sample can be a clinical sample, an environmental sample or a research sample. Clinical samples can include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Research samples can include cultured cells, primary cells, bacteria, spores, viruses, small organisms, any of the clinical samples listed above. Samples can be collected for diagnostic purposes (e.g., the quantitative measurement of a clinical analyte such as an infectious agent) or for monitoring purposes (e.g., to monitor the course of a disease or disorder). For example, samples of polynucleotides may be collected or obtained from a subject having a disease or disorder, at risk of having a disease or disorder, or suspected of having a disease or disorder.

Nucleic acid samples provided in this disclosure can be derived from an organism. In some embodiments, an entire organism may be used. In some embodiments, portion of an organism may be used. For example, a portion of an organism may include an organ, a piece of tissue comprising multiple tissues, a piece of tissue comprising a single tissue, a plurality of cells of mixed tissue sources, a plurality of cells of a single tissue source, a single cell of a single tissue source, cell-free nucleic acid from a plurality of cells of mixed tissue source, cell-free nucleic acid from a plurality of cells of a single tissue source and cell-free nucleic acid from a single cell of a single tissue source and/or body fluids. In some embodiments, the portion of an organism is a compartment such as mitochondrion, nucleus, or other compartment described herein. In some embodiments, the portion of an organism is cell-free nucleic acids present in a fluid, e.g., circulating cell-free nucleic acids.

A tissue can be derived from any of the germ layers. In some embodiments, the germ layers may be neural crest, endoderm, ectoderm and/or mesoderm. The germ layers may give rise to any of the following tissues, connective tissue, skeletal muscle tissue, smooth muscle tissue, nervous system tissue, epithelial tissue, ectodermal tissue, endodermal tissue, mesodermal tissue, endothelial tissue, cardiac muscle tissue, brain tissue, spinal cord tissue, cranial nerve tissue, spinal nerve tissue, neuron tissue, skin tissue, respiratory tissue, reproductive tissue and/or digestive tissue. In some embodiments, the organ can be derived from any of the germ layers. In some embodiments, the germ layers may give rise to any of the following organs, adrenal glands, anus, appendix, bladder, bones, brain, bronchi, ears, esophagus, eyes, gall bladder, genitals, heart, hypothalamus, kidney, larynx, liver, lungs, large intestine, lymph nodes, meninges, mouth, nose, pancreas, parathyroid glands, pituitary gland, rectum, salivary glands, skin, skeletal muscles, small intestine, spinal cord, spleen, stomach, thymus gland, thyroid, tongue, trachea, ureters and/or urethra. In some embodiments, the organ may contain a neoplasm. In some embodiments, the neoplasm may be a tumor. In some embodiments, the tumor may be cancer. In some embodiments, the sample may comprise a tumor sample. In some embodiments, the sample may comprise malignant B cells. In some embodiments, the sample may comprise malignant T cells. In some embodiments, the sample may comprise cells, and the cells may be derived from a tissue having a disease. In some embodiments, the disease may be a leukemia. In some embodiments, the disease may be a lymphoma.

A cell can be derived from any tissue. In some embodiments, the cell may include exocrine secretory epithelial cells, hormone secreting cells, keratinizing epithelial cells, wet stratified barrier epithelial cells, sensory transducer cells, autonomic neuron cells, sense organ and peripheral neuron supporting cells, central nervous system neurons, glial cells, lens cells, metabolism and storage cells, kidney cells, extracellular matrix cells, contractile cells, blood and immune system cells, germ cells, nurse cells and/or interstitial cells.

Body fluids may be suspensions of biological particles in a liquid. For example, a body fluid may be blood. In some embodiments, blood may include plasma and/or cells (e.g., red blood cells, white blood cells, or circulating rare cells) and/or platelets. In some embodiments, a blood sample contains blood that has been depleted of one or more cell types. In some embodiments, a blood sample contains blood that has been enriched for one or more cell types. In some embodiments, a blood sample contains a heterogeneous, homogenous or near-homogenous mix of cells. Body fluids can include, for example, whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolymph, peritoneal fluid, pleural fluid, cerumen, epicardial fluid, and secretions of the respiratory, intestinal and/or genitourinary tracts. In some embodiments, body fluids can be in contact with various organs (e.g. lung) that contain mixtures of cells.

Body fluids can contain at least one cell. Cells may include, for example, cells of a malignant phenotype; fetal cells (e.g., fetal cells in maternal peripheral blood); tumor cells, (e.g., tumor cells which have been shed from tumor into blood and/or other bodily fluids); cancerous cells; immortal cells; stem cells; cells infected with a virus, (e.g., cells infected by HIV); cells transfected with a gene of interest; aberrant subtypes of T-cells and/or B-cells present in the peripheral blood of subjects afflicted with autoreactive disorders. In some embodiments, the cell may be one of the following, erythrocytes, white blood cells, leukocytes, lymphocytes, B cells, T cells, mast cells, monocytes, macrophages, neutrophils, eosinophils, dendritic cells, stem cells, erythroid cells, cancer cells, tumor cells or cell isolated from any tissue originating from the endoderm, mesoderm, ectoderm and/or neural crest tissues. Cells may be from a primary source and/or from a secondary source (e.g., a cell line). The body fluids may also contain polynucleotides, e.g., cell-free fetal polynucleotides or DNA circulating in maternal blood.

The nucleic acids within a sample may be located within a region of a cell or a cellular compartment. The region or compartment of a cell may include a membrane, an organelle and/or the cytosol. For example, the membranes may include, but are not limited to, nuclear membrane, plasma membrane, endoplasmic reticulum membrane, cell wall, cell membrane and/or mitochondrial membrane. The membranes may include a complete membrane or a fragment of a membrane. For example, the organelles may include, but are not limited to, the nucleolus, nucleus, chloroplast, plastid, endoplasmic reticulum, rough endoplasmic reticulum, smooth endoplasmic reticulum, centrosome, golgi apparatus, mitochondria, vacuole, acrosome, autophagosome, centriole, cilium, eyespot apparatus, glycosome, glyoxysome, hydrogenosome, lysosome, melanosome, mitosome, myofibril, parenthesome, peroxisome, proteasome, ribosome, vesicle, carboxysome, chlorosome, flagellum, magenetosome, nucleoid, plasmid, thylakoid, mesosomes, cytoskeleton, and/or vesicles. In some embodiments, the organelles may include a complete membrane or a fragment of a membrane. For example, the cytosol may be encapsulated by the plasma membrane, cell membrane and/or the cell wall.

A sample may comprise nucleic acids that are not bound to protein. The nucleic acids may be treated with an agent to reduce protein binding, remove bound proteins and/or prevent protein binding. In some embodiments, the agent may be a chemical agent, a source of temperature change, a source of sound energy, a source of optical energy, a source of light energy, and/or a source of heat energy. In some embodiments, the chemical agent may be an enzyme. In some embodiments, the enzyme may cleave the bonds between amino acids of a protein.

Samples comprising nucleic acids may comprise deoxyribonucleic acid (DNA), genomic DNA, mitochondrial DNA, complementary DNA, synthetic DNA, plasmid DNA, viral DNA, linear DNA, circular DNA, double-stranded DNA, single-stranded DNA, digested DNA, fragmented DNA, ribonucleic acid (RNA), small interfering RNA, messenger RNA, transfer RNA, micro RNA, duplex RNA, double-stranded RNA and/or single-stranded RNA.

In some embodiments, nucleic acid (e.g., genomic DNA) may be the entire genome of a species, such as viruses, yeast, bacteria, animals, and plants. The nucleic acid (e.g., genomic DNA) may be from still higher life forms (e.g., human genomic DNA). In some embodiments, the nucleic acid (e.g., genomic DNA) may comprise one or more chromatid fibers, or at least 25%, 50%, 75%, 80%, 90%, 95%, or 98% of the nucleic acid (e.g., genomic DNA) of the species or of an organism or cell.

In some embodiments, the nucleic acid may contain the nucleic acid sequence of a heavy chain or a light chain of an antibody or a fragment thereof. In some embodiments, the nucleic acid may contain the nucleic acid sequence of more than one heavy chain or light chain of an antibody or a fragment thereof. For example, the antibody may be of any type, but not limited to, IgA, IgD, IgE, IgG, IgY or IgM. The nucleic acid may contain the sequence of more than one antibody where each antibody is of the same subtype. The nucleic acid may contain the sequence of more than one antibody where each antibody is a different subtype.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains (Fc) that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

The terms "antigen-binding portion of an antibody," "antigen-binding fragment", "antigen-binding domain", "antibody fragment" or a "functional fragment of an antibody" are used interchangeably in the present disclosure, and may generally refer to one or more fragments of an antibody that retain the ability to specifically bind to an antigen. Non-limiting examples of antibody fragments included within, but not limited to, the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (e.g., single chain Fv (scFv)). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and VL can also be used in the generation of Fab, Fv or other fragments of immunoglobulins using either protein chemistry or recombinant DNA technology. Other forms of single chain antibodies, such as diabodies are also encompassed.

"F(ab')2" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CHγ1 (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for antigen binding.

In some embodiments, the nucleic acid may contain a part of the antibody. For example, the part of the antibody may be a complementary determining region (CDR), variable fragment (Fv), ab fragment (Fab) or crystallizable fragment (Fc).

Libraries

As used herein, "library" refers to a plurality of polynucleotides, proteins, or cells comprising a collection of two, or two or more, non-identical but related members. In some embodiments, a library may be a complex library. A "synthetic library" refers to a plurality of synthetic polynucleotides, or a population of cells that comprise said plurality of synthetic polynucleotides. A "semi-synthetic library" refers to a plurality of semi-synthetic polynucleotides, or a population of cells that comprise said plurality of semi-synthetic polynucleotides.

Static libraries are typically limited in their size and scope. Phage display libraries, for example can display as many as $10^{12}$ members, and ribosomal libraries have been constructed that potentially contain ~$10^{16}$ members. Libraries presented on the surface of bacterial and mammalian cells are not usually this complex, typically with fewer than $10^9$ members. In addition, robust library construction and selection usually requires that libraries contain several fold redundancy, which further limits this theoretically complexity, and makes screening the entire library slow, expensive, and in some cases impractical.

Despite these levels of complexity, such static libraries can explore only a small fraction of possible sequence space, i.e., the potential number of possible permutations within a polynucleotide region of interest. For example, a heavy chain IgG sequence may contain more than 30 amino acids within the CDR1, CDR2, and CDR3 complementarity regions, giving this single chain more than $20^{30}$ possible permutations, dwarfing even the largest of potential static libraries. Because of this limitation, researchers have explored methodologies for evolving protein sequences and libraries.

In the disclosure provided herein, libraries of samples may be generated by cloning the antibody fragments amplified by a single primer at engineered restriction sites including, but not limited to, XbaI, BspEI, SalI, XhoI, SalI, and AgeI, into suitable vectors for phage display, bacterial expression, and mammalian expression. Other restriction sites are described below and are considered for use in the methods described herein.

This library can have the following properties: i) The construction of libraries is easy especially when the preparation of template is multiplexed with mixed primers. ii) The library is potentially more diverse covering unbiased antibody repertoire up to $10^{10}$ to $10^{12}$ compared to the ones made using traditional PCR method. Traditional PCR amplification requires two gene-specific primers that have different annealing temperatures that are often problematic to optimize. This leads biased amplification and non-specific amplification and results in poor quality in the constructed libraries. iii) As the potential diversity is higher, as shown in the example, multiple antigens can be used to immunize one mouse and a single library can be used to isolate large panel of antibodies to each antigen.

In some embodiments, the types of libraries may include Fab, F(ab')$_2$, scFv fragments of antibodies from non-human subjects (e.g., mouse, rat, rabbit, human, chicken, shark, llama, horse, monkeys, goats, frogs, or fish). In some embodiments, the libraries may include humanized scFv fragments of antibodies from non-human subjects (e.g., mouse, rat, rabbit, human, chicken, shark, llama, horse, monkeys, goats, frogs, or fish).

Cell based expression systems include any suitable prokaryotic or eukaryotic expression system. In certain embodiments, the preferred cell-based expression systems are those that can be easily and reliably grown, have reasonably fast growth rates, have well characterized expression systems and can be transformed or transfected easily and efficiently.

Phage Display

In some embodiments of the present disclosure, a library or complex library may comprise a phage display library. "Phage display" is a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations.

A "phagemid" is a plasmid vector having a bacterial origin of replication, e.g., ColE1, and a copy of an intergenic region of a bacteriophage. Phagemids may be used on any known bacteriophage, including filamentous bacteriophage and lambdoid bacteriophage. Generally, the plasmid will also contain a selectable marker for antibiotic resistance. Segments of DNA cloned into these vectors can be propagated as plasmids. When cells harboring vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids, which contain a phage coat protein gene or fragment thereof linked to a heterologous polypeptide gene as a gene fusion such that the heterologous polypeptide is displayed on the surface of the phage particle.

The term "phage vector" may be used to refer to a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

The term "coat protein" means a protein, at least a portion of which is present on the surface of the virus particle. From a functional perspective, a coat protein is any protein, which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at preferably at least about 5, more preferably at least about 7, even more preferably at least about 10 copies of the protein or more. A major coat protein may be present in tens, hundreds or even thousands of copies per virion. An example of a major coat protein is the p8 protein of filamentous phage.

Prokaryotic Expression Systems

Within these general guidelines, useful microbial hosts include bacteria from the genera *Bacillus, Escherichia* (such as *E. coli*), *Pseudomonas, Streptomyces, Salmonella, Erwinia, Bacillus subtilis, Bacillus brevis,* the various strains of *Escherichia coli* (e.g., HB101, (ATCC NO. 33694) DH5α, DH10, and MC1061 (ATCC NO. 53338)).

Eukaryotic Expression Systems

Yeast—

Many strains of yeast cells known to those skilled in the art are also available as host cells for the expression of polypeptides including those from the genera *Hansenula, Kluyveromyces, Pichia, Rhino-sporidium, Saccharomyces,* and *Schizosaccharomyces,* and other fungi. Preferred yeast cells include, for example, *Saccharomyces cerivisae* and *Pichia pastoris.*

Insect Cells—

Additionally, where desired, insect cell systems can be utilized in the methods of the present disclosure. Preferred insect cells include Sf-9 and HI5 (Invitrogen, Carlsbad, Calif.).

Mammalian Cells—

A number of suitable mammalian host cells are also known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., *Proc. Natl. Acad. Sci. USA,* 97:4216-4220 (1980)), human embryonic kidney (HEK) 293 or 293T cells (ATCC No. CRL1573), PER.C6™ cells, or 3T3 cells (ATCC No. CCL92). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells can be genotypically deficient in the selection gene, or may contain a dominantly acting selection gene. Other suitable mammalian cell lines include, but are not limited to, mouse neuroblastoma N2A cells, HeLa, mouse L-929 cells, 3T3 lines derived from Swiss, BALB/c or NIH mice, BHK or HaK hamster cell lines, which are available from the ATCC. Each of these cell lines is known by and available for protein expression.

Also of interest are lymphoid, or lymphoid derived cell lines, such as a cell line of pre-B lymphocyte origin. Specific examples include without limitation RAMOS (CRL-1596), Daudi (CCL-213), EB-3 (CCL-85), DT40 (CRL-2111), 18-81, (Jack et al., *PNAS USA* (1988) 85 1581-1585), Raji cells, (CCL-86) and derivatives thereof.

Representative commercially available viral expression vectors include, but are not limited to, the adenovirus-based Per.C6 system available from Crucell, Inc., the lentiviral-based pLP1 from Invitrogen, and the Retroviral Vectors pFB-ERV plus pCFB-EGSH from Stratagene.

An episomal expression vector suitable for the expression of the libraries described herein is able to replicate in the host cell, and persists as an extrachromosomal episome within the host cell in the presence of appropriate selective pressure. (See for example, Conese et al., *Gene Therapy* 11 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP), specific examples include the vectors pREP4, pCEP4, pREP7 from Invitrogen. The vectors pcDNA3.1 from Invitrogen, and pBK-CMV from Stratagene represent non-limiting examples of an episomal vector that uses T-antigen and the SV40 origin of replication in lieu of EBNA1 and oriP.

In some embodiments of the present disclosure, a library may be used to select one or more fragment antigen-binding (fAb) domains that have an affinity (e.g., a high affinity) for a clonal lineage specific marker protein (CLSMP). For example, after obtaining a tumor sample from a subject, next generation sequencing may be performed to determine the sequence of a CLSMP expressed by cells derived from the tumor. Following sequencing, the CLSMP may be expressed as a protein, immobilized on a substrate (e.g., in the form of an array), and contacted with a plurality of fAb domains selected from a complex library to determine which fAb(s) may have a high binding affinity for the CLSMP. After identifying one or more fAbs having an affinity for binding the CLSMP, a construct or antibody having the identified fAb may be produced.

Oligonucleotides

An oligonucleotide may be used in the methods described herein (e.g., for sequencing a sample from a subject, or preparing a library). In some embodiments, one oligonucleotide may be used. In some embodiments, more than one oligonucleotide may be used. For example, 1, 2, 3, 4, 5, 6, 7, 8, 9, or 10 oligonucleotides may be used. In some embodiments, more than 10 oligonucleotides may be used. For example, a first, a second, a third, a fourth, a fifth, a sixth, a seventh, an eighth, a ninth and/or a tenth oligonucleotide may be used. In some embodiments, an oligonucleotide may be an adaptor oligonucleotide. In some embodiments, the adaptor oligonucleotides may be annealed together prior to annealing the adaptor oligonucleotides to the polynucleotide. In some embodiments, the adaptor oligonucleotides may be annealed together prior to ligating the adaptor oligonucleotides to the polynucleotide.

In some embodiments, the oligonucleotide may contain a plurality of nucleotides. For example, an oligonucleotide may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or 100 nucleotides. In some embodiments, an oligonucleotide may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or more than 100 nucleotides. In some embodiments, an oligonucleotide may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or less than 100 nucleotides.

In some embodiments, an oligonucleotide may contain a desired sequence. In some embodiments, an oligonucleotide may contain more than one desired sequence. For example, a desired sequence may be a restriction endonuclease restriction site, a pre-determined sequence, a complementary sequence, a known sequence, a primer binding sequence, a universal sequence, or a detection sequence. In some embodiments, a pre-determined sequence may be a universal sequence.

In some embodiments, a plurality of oligonucleotides may be used to add more than one desired sequence to a polynucleotide to create the engineered template. In some embodiments, the desired sequence may be a predetermined sequence. For example, the predetermined sequence may be a first, second, third, fourth, fifth, sixth, seventh, eighth, ninth or tenth predetermined sequence. In some embodiments, any predetermined sequence within the oligonucleotide may be disposed near the 5' end of the oligonucleotide. In some embodiments, any predetermined sequence within the oligonucleotide may be disposed near the 3' end of the oligonucleotide. In some embodiments, any predetermined sequence within the oligonucleotide may be disposed near the middle of the oligonucleotide. In some embodiments, a first predetermined sequence of the oligonucleotide may be disposed near the 5' end of the oligonucleotide. In some embodiments, a first predetermined sequence of the oligonucleotide may be disposed near the 3' end of the oligonucleotide. In some embodiments, a first predetermined sequence of the oligonucleotide may be disposed near the middle of the oligonucleotide. In some embodiments, a second predetermined sequence of the oligonucleotide may be disposed near the 5' end of the oligonucleotide. In some embodiments, a second predetermined sequence of the oligonucleotide may be disposed near the 3' end of the oligonucleotide. In some embodiments, a second predetermined sequence of the oligonucleotide may be disposed near the middle of the oligonucleotide. In some embodiments, a third predetermined sequence of the oligonucleotide may be disposed near the 5' end of the oligonucleotide. In some embodiments, a third predetermined sequence of the oligonucleotide may be disposed near the 3' end of the oligonucleotide. In some embodiments, a third predetermined sequence of the oligonucleotide may be disposed near the middle of the oligonucleotide.

In some embodiments, the first pre-determined sequence and the second pre-determined sequence are not substantially similar to any sequence within the first or the second polynucleotide.

In some embodiments, the desired sequence may be any length of nucleotides less than the length of the oligonucleotide. For example, the desired sequence may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the desired sequence may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the desired sequence may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The oligonucleotide may contain nucleotides which bind to a polynucleotide. In some embodiments, nucleotides which bind to a polynucleotide contained within the oligonucleotide may be located at any site within the oligonucleotide. In some embodiments, the nucleotides which bind to a polynucleotide may be at the 3' end of the oligonucleotide. In some embodiments, the nucleotides which bind to a polynucleotide may be at the 5' end of the oligonucleotide. In some embodiments, the nucleotides which bind to a polynucleotide may be substantially near the 3' end of the oligonucleotide. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments, the nucleotides which bind to a polynucleotide may be substantially near the 5' end of the oligonucleotide. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments the nucleotides which bind to a polynucleotide may be in the middle of the oligonucleotide.

In some embodiments, the nucleotides which bind to a polynucleotide may be any length of nucleotides less than the length of the oligonucleotide. For example, the nucleotides which bind to a polynucleotide may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the nucleotides which bind to a polynucleotide may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the nucleotides which bind to a polynucleotide may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The nucleotides which bind to a polynucleotide contained within the oligonucleotide may be located at any site within the oligonucleotide. In some embodiments, the nucleotides which bind to a polynucleotide may be at the 3' end of the oligonucleotide. In some embodiments, the nucleotides which bind to a polynucleotide may be at the 5' end of the oligonucleotide. In some embodiments, the nucleotides which bind to a polynucleotide may be substantially near the 3' end of the oligonucleotide. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments, the nucleotides which bind to a polynucleotide may be substantially near the 5' end of the oligonucleotide. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments, the nucleotides which bind to a polynucleotide may be in the middle of the oligonucleotide.

In some embodiments, the oligonucleotide may have one portion. In some embodiments, the oligonucleotide may have more than one portion. For example, the oligonucleotide may have a first, second, third, fourth, fifth, sixth, seventh, eighth, ninth or tenth portion. In some embodiments, any portion of the oligonucleotide may be disposed near the 5' end of the oligonucleotide. In some embodiments, any portion of the oligonucleotide may be disposed near the 3' end of the oligonucleotide. In some embodiments, any portion of the oligonucleotide may be disposed near the middle of the oligonucleotide. In some embodiments, a first portion of the oligonucleotide may be disposed near the 5' end of the oligonucleotide. In some embodiments, a first portion of the oligonucleotide may be disposed near the 3' end of the oligonucleotide. In some embodiments, a first portion of the oligonucleotide may be disposed near the middle of the oligonucleotide. In some embodiments, a second portion of the oligonucleotide may be disposed near the 5' end of the oligonucleotide. In some embodiments, a second portion of the oligonucleotide may be disposed near the 3' end of the oligonucleotide. In some embodiments, a second portion of the oligonucleotide may be disposed near the middle of the oligonucleotide. In some embodiments, a third portion of the oligonucleotide may be disposed near the 5' end of the oligonucleotide. In some embodiments, a third portion of the oligonucleotide may be disposed near the 3' end of the oligonucleotide. In some embodiments, a third portion of the oligonucleotide may be disposed near the middle of the oligonucleotide.

In some embodiments, a polynucleotide may be contacted with at least one oligonucleotide containing a desired sequence. In some embodiments, the oligonucleotide may be, but not limited to, hybridized, annealed or ligated to the polynucleotide. For example, the oligonucleotide with the desired sequence (e.g., a predetermined sequence) may be ligated to the polynucleotide using an enzyme. For example, the enzyme may be a ligase (e.g., a DNA ligase). In some embodiments, the oligonucleotide containing a predetermined sequence may be ligated to the 3' end or the 5' end of the polynucleotide. In some embodiments, more than one pre-determined sequence may be ligated to the polynucleotide. For example, a first pre-determined sequence may be ligated to one end of the polynucleotide and a second pre-determined sequence may be ligated to the other end of the polynucleotide. In some embodiments, the first pre-determined sequence may be complementary to the second pre-determined sequence. In some embodiments, the first pre-determined sequence may be reverse complementary to the second pre-determined sequence. In some embodiments, the first pre-determined sequence may not be complementary to the second pre-determined sequence.

In some embodiments, the addition of at least one pre-determined sequence to a polynucleotide may create a template (e.g., an engineered template). For example, the template may be used in any method designed to amplify the polynucleotide within the template. The pre-determined sequence may be used in primer amplification of the polynucleotide. In some embodiments, a single primer may be annealed to at least one pre-determined sequence located on the polynucleotide. In other embodiments, more than one primer may be annealed to at least one pre-determined sequence located on the polynucleotide.

In some embodiments, a restriction endonuclease restriction site may be located within the oligonucleotide. For example, the restriction endonuclease restriction site may be any site which is recognized by a restriction endonuclease where the restriction endonuclease restriction site within the oligonucleotide is a restriction endonuclease restriction site native to the polynucleotide. For example, any sites recognized by any one of the following restriction endonucleases, but not limited to the following, may be used; Aar I, Ban II, BseG I, BspP I, Cfr I, EcoN I, Hsp92 II, Nla IV, Rsa I, Tai I, Aas I, Bbs I, BseJ I, BspT I, Cla I, EcoO109 I, I-Ppo I, NmuC I, Rsr II, Taqa I, Aat II, Bbu I, BseL I, BsrB I, Cpo I, EcoR I, Kas I, Not I, Sac I, Taq I, Acc65 I, BbvC I, BseM I, BsrD I, Csp45 I, EcoR V, Kpn2 I, Nru I, Sac II, Tas I, AccB7 I, Bbv I, BseM II, BsrF I, Csp6 I, Ehe I, Kpn I, Nsb I, Sal I, Tat I, Acc I, BceA I, BseN I, BsrG I, Csp I, Esp3 I, KspA I, Nsi I, Sap I, Tau I, Acc III, Bcg I, BseR I, Bsr I, Dde I, Fau I, Lwe I, Nsp I, Sat I, Tfi I, Aci I, Bci VI, BseS I, BsrS I, Dpn I, Fnu4H I, Mbi I, Oli I, Sau3A I, Tli I, ACL I, BCL I, BseX I, BssH II, Dpn II, Fok I, Mbo I, Pac I, Sau96 I, Trul I, Ade I, Bcn I, BseY I, BssK I, Dra I, Fse I, Mbo II, Pae I, Sbf I, Tru9 I, Afe I, Bcu I, Bsg I, BssS I, Dra III, FspA I, Mfe I, PaeR7 I, Sca I, Tse I, Afl II, Bfa I, Bsh1236 I, Bst1107 I, Drd I, Fsp I, Mls I, Pag I, Sch I, Tsp45 I, Afl III, Bfi I, Bsh1285 I, Bst98 I, Eae I, Gsu I, Mlu I, Pau I, ScrF I, Tsp509 I, Age I, Bfm I, BshN I, BstAP I, Eag I, Hae II, Mly I, Pci I, Sda I, TspR I, Ahd I, BfrB I, BshT I, BstB I, Eam1104 I, Hae III, Mme I, Pdi I, Sdu I, Tth111 I, Ale I, BfuA I, BsiE I, BstE II, Eam1105 I, Hga I, Mnl I, Pdm I, SexA I, TurboNae I, Alo I, BfuC I, BsiHKA I, BstF5 I, Ear I, Hha I, Mph1103 I, Pfl23 II, SfaN I, TurboNar I, Alu I, Bfu I, BsiW I, BstN I, Eci I, Hin1 I, Msc I, PflF I, Sfc I, Van91 I, Alw21 I, Bgl I, Bsl I, BstO I, Ecl136 II, Hin4 I, Mse I, PflM I, Sfi I, Vsp I, Alw26 I, Bgl II, BsmA I, BstU I, EclHK I, Hin6 I, Ms1 I, Pfo I, Sfo I, Xag I, Alw44 I, Blp I, BsmB I, BstX I, Eco105 I, Hinc II, MspA1 I, Ple I, Sgf I, Xap I, Alw I, Bme1390 I, BsmF I, BstY I, Eco130 I, Hind III, Msp I, Pme I, SgrA I, Xba I, AlwN I, Box I, Bsm I, BstZ I, Eco147 I, Hinf I, Mss I, Pml I, Sin I, Xce I, Apa I, Bpi I, BsoB I, Bsu15 I, Eco24 I, HinP1 I, Mun I, Ppi I, Sma I, Xcm I, ApaL I, Bpi I, Bsp119 I, Bsu36 I, Eco31 I, Hpa I, Mva1269 I, PpuM I, Smi I, Xho I, Apo I, Bpu10 I, Bsp120 I, BsuR I, Eco32 I, Hpa II, Mva I, PshA I, Sml I, Xho II, Asc I, Bpu1102 I, Bsp1286 I, Btg I, Eco47 I, Hph I, Mwo I, Psi I, Smu I, Xma I, Ase I, BsaA I, Bsp1407 I, Bts I, Eco47 III, Hpy188 I, Nae I, Psp1406 I, SnaB I, XmaJ I, AsiS I, BsaB I, Bsp143 I, Bve I, Eco52 I, Hpy188 III, Nar I, Psp5 II, Spe I, Xmi I, Ava I, BsaH I, Bsp143 II, Cac8 I, Eco57 I, Hpy8 I, Nci I, PspG I, Sph I, Xmn I, Ava II, Bsa I, Bsp68 I, Cal I, Eco57M I, Hpy99 I, Nco I, PspOM I, Ssp I, Avr II, BsaJ I, BspD I, Cfo I, Eco72 I, HpyCH4 III, Nde I, Pst I, Stu I, Bae I, BsaM I, BspE I, Cfr10 I Eco81 I HpyCH4 IV, Nde II, Psu I, StyD4 I, Bal I, BsaW I, BspH I, Cfr13 I, Eco88 I, HpyCH4 V, NgoM IV, Psy I, Sty I, BamH I, BsaX I, BspL I, Cfr42 I, Eco91 I, HpyF10 VI, Nhe I, Pvu I, Swa I, Ban I, BseD I, BspM I, Cfr9 I, EcoICR I, Hsp92 I, Nla III, Pvu II, Taa I, Bln I, and PspX I.

In some embodiments, the restriction site may be unique to one restriction endonuclease. In some embodiments, the restriction site may be recognized by more than one restriction endonuclease. In some embodiments, the restriction site may be recognized by a blunt-cut restriction endonuclease. In some embodiments, the restriction site may be recognized by a sticky-cut restriction endonuclease.

Primers

In the disclosure provided herein, at least one primer may be used (e.g., for sequencing a sample from a subject, or to prepare a library). In some embodiments, one primer may be used. In some embodiments, more than one primer may be used. For example, 1, 2, 3, 4, 5, 6, 7, 8, 9, or 10 primers may be used. In some embodiments, more than 10 primers may be used. For example, a first, a second, a third, a fourth, a fifth, a sixth, a seventh, an eighth, a ninth and/or a tenth primer may be used.

In some embodiments, the primer may contain a plurality of nucleotides. For example, a primer may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or 100 nucleotides. In some embodiments, a primer may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or more than 100 nucleotides. In some embodiments, a primer may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or less than 100 nucleotides.

In some embodiments, a primer may contain a desired sequence. In some embodiments, a primer may contain more than one desired sequence. For example, a desired sequence may be a pre-determined sequence, a complementary sequence, a known sequence, a binding sequence, a universal sequence, or a detection sequence. In some embodiments, a pre-determined sequence may be a universal sequence.

In some embodiments, the desired sequence may be any length of nucleotides less than the length of the primer. For example, the desired sequence may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the desired sequence may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the desired sequence may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The primer may contain nucleotides which bind to a polynucleotide. In some embodiments, nucleotides which bind to a polynucleotide contained within the primer may be located at any site within the primer. In some embodiments, the nucleotides which bind to a polynucleotide may be at the 3' end of the primer. In some embodiments, the nucleotides which bind to a polynucleotide may be at the 5' end of the primer. In some embodiments, the nucleotides which bind to a polynucleotide may be substantially near the 3' end of the primer. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer. In some embodiments, the nucleotides which bind to a polynucleotide may be substantially near the 5' end of the primer. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer. In some embodiments the nucleotides which bind to a polynucleotide may be in the middle of the primer.

In some embodiments, the nucleotides which bind to a polynucleotide may be any length of nucleotides less than the length of the primer. For example, the nucleotides which bind to a polynucleotide may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the nucleotides which bind to a polynucleotide may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the nucleotides which bind to a polynucleotide may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The nucleotides which bind to a polynucleotide contained within the primer may be located at any site within the primer. In some embodiments, the nucleotides which bind to a polynucleotide may be at the 3' end of the primer. In some embodiments, the nucleotides which bind to a polynucleotide may be at the 5' end of the primer. In some embodiments, the nucleotides which bind to a polynucleotide may be substantially near the 3' end of the primer. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer. In some embodiments, the nucleotides which bind to a polynucleotide may be substantially near the 5' end of the primer. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer. In some embodiments, the nucleotides which bind to a polynucleotide may be in the middle of the primer.

In some embodiments, a polynucleotide may be contacted with at least one primer containing a desired sequence. In some embodiments, the primer may be, but not limited to, hybridized or annealed to the polynucleotide. For example, the primer with the desired sequence (e.g., predetermined sequence) may be used to amplify the polynucleotide using an enzyme. For example, the enzyme may be a polymerase (e.g., a Taq polymerase). In some embodiments, the primer containing a predetermined sequence may be annealed or hybridized to the 3' end or the 5' end of the polynucleotide. In some embodiments, more than one pre-determined sequence may be annealed or hybridized to the polynucleotide. For example, a first pre-determined sequence may be annealed or hybridized to one end of the polynucleotide and a second pre-determined sequence may be annealed or hybridized to the other end of the polynucleotide. In some embodiments, the first pre-determined sequence may be complementary to the second pre-determined sequence. In some embodiments, the first pre-determined sequence may be reverse complementary to the second pre-determined sequence. In some embodiments, the first pre-determined sequence may not be complementary to the second pre-determined sequence.

In some embodiments, at least one oligonucleotide and at least one primer may be used to create a template from a polynucleotide such that the polynucleotide contains more than one pre-determined sequence. In some embodiments, only oligonucleotides may be used to create a template from a polynucleotide such that the polynucleotide contains more than one pre-determined sequence. In some embodiments, only primers may be used to create a template from a polynucleotide such that the polynucleotide contains more than one pre-determined sequence.

Nucleic Acid Molecules

The present disclosure also provides nucleic acid molecules encoding one or more BFP or TFP constructs. In one aspect, the nucleic acid molecule is provided as a messenger RNA transcript. In one aspect, the nucleic acid molecule is provided as a DNA construct.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present disclosure also provides vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired BFP or TFP of the present disclosure is an adenoviral vector (A5/35). In another embodiment, the expression of nucleic acids encoding BFPs or TFPs can be accomplished using of transposons such as sleeping beauty, crisper, CAS9, and zinc finger nucleases.

The expression constructs of the present disclosure may also be used for nucleic acid immunization and gene therapy, using standard gene delivery protocols. Methods for gene delivery are known in the art. In another embodiment, the present disclosure provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers.

A number of virally based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a TFP transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving TFP expression from transgenes cloned into a lentiviral vector. Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline-regulated promoter.

In order to assess the expression of a BFP or TFP polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. For example, one method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20 C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure.

The present disclosure further provides a vector comprising a nucleic acid molecule encoding a BFP or TFP. In one aspect, a BFP or a TFP vector can be directly transduced into a cell (e.g., a B cell or a T cell). In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the TFP construct in mammalian T cells. In one aspect, the mammalian T cell is a human T cell.

Cell Samples

Prior to expansion and genetic modification, a source of B cells or T cells may be obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present disclosure, any commercially available or subject-generated B cell or T cell (or cell lines) may be used. In certain aspects of the present disclosure, B cells or T cells can be obtained from a unit of blood collected from a subject using any number of techniques known to the person having skill in the art, such as Ficoll separation. In one preferred aspect, cells from the circulating blood of a subject are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the present disclosure, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In some aspects, cells, antibodies, or constructs may be obtained, isolated, and/or purified using hybridoma technology. Hybridoma technology is a method for producing large numbers of identical antibodies. This process may comprise injecting a subject (e.g., a mouse) with an antigen that provokes an immune response. A type of white blood cell, the B cell that produces antibodies that bind to the antigen are then harvested from the subject. These isolated B cells are in turn fused with immortal B cell cancer cells, a myeloma, to produce a hybrid cell line called a hybridoma, which has both the antibody-producing ability of the B-cell and the exaggerated longevity and reproductivity of the myeloma. The hybridomas can be grown in culture, each culture starting with one viable hybridoma cell, producing cultures each of which consists of genetically identical hybridomas which produce one antibody per culture (monoclonal) rather than mixtures of different antibodies (polyclonal).

In one aspect, cells are isolated from peripheral blood lymphocytes by lysing the red blood cells and depleting the monocytes, for example, by centrifugation through a PER-COLL™ gradient or by counterflow centrifugal elutriation. A specific subpopulation of B cells or T cells, such as CD3+, CD4+, CD5+, CD8+, CD19+, CD22−, CD23+, CD28+, CD45RA+, CD45RO+, and/or FMC7+ B cells or T cells, can be further isolated by positive or negative selection techniques. For example, in one aspect, B cells are isolated by incubation with anti-CD5/anti-CD19 (e.g., 5×19)-conjugated beads for a time period sufficient for positive selection of the desired B cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate B cells in any situation where there are few B cells as compared to other cell types. Additionally, by increasing or decreasing the ratio of anti-CD5 and/or anti-CD19 antibodies on the beads or other surface, subpopulations of B cells can be preferentially selected for or against at culture initiation or at other desired time points. The person having skill in the art would recognize that multiple rounds of selection can also be used. In certain aspects, it may be desirable to perform the selection procedure and use the "unselected" cells in the activation and expansion process. "Unselected" cells can also be subjected to further rounds of selection.

Enrichment of a B cell or T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, or from samples where there are many tumor cells present (e.g., leukemic blood, tumor tissue, etc.). Such populations of cells may have therapeutic value and would be desirable to obtain.

Also contemplated in the context of the present disclosure is the collection of blood samples or apheresis product from a subject at a time period prior to when the ells as described herein might be needed. As such, the source of the cells may be collected at any time point necessary, and desired cells, such as B cells or T cells, isolated and frozen for later use in B cell or T cell therapy for any number of diseases or conditions that would benefit from a cell therapy, such as methods described herein.

Activation and Expansion of B Cells and T Cells

Generally, the T cells of the present disclosure may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once an anti-CD19 TFP is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of an anti-CD19 TFP are described in further detail below Western blot analysis of TFP expression in primary T cells can be used to detect the presence of monomers and dimers. Very briefly, T cells (1:1 mixture of CD4$^+$ and CD8$^+$ T cells) expressing the TFPs are expanded in vitro for more than 10 days followed by lysis and SDS-PAGE under reducing conditions. TFPs are detected by Western blotting using an antibody to a TCR chain. The same T cell subsets are used for SDS-PAGE analysis under non-reducing conditions to permit evaluation of covalent dimer formation.

In vitro expansion of TFP$^+$ T cells following antigen stimulation can be measured by flow cytometry. For example, a mixture of CD4$^+$ and CD8$^+$ T cells are stimulated with alphaCD3/alphaCD28 and APCs followed by transduction with lentiviral vectors expressing GFP under the control of the promoters to be analyzed. Exemplary promoters include the CMV IE gene, EF-1alpha, ubiquitin C, or phosphoglycerokinase (PGK) promoters. GFP fluorescence is evaluated on day 6 of culture in the CD4+ and/or CD8+ T cell subsets by flow cytometry. See, e.g., Milone et al., Molecular Therapy 17(8): 1453-1464 (2009). Alternatively, a mixture of CD4+ and CD8+ T cells are stimulated with alphaCD3/alphaCD28 coated magnetic beads on day 0, and transduced with TFP on day 1 using a bicistronic lentiviral vector expressing TFP along with eGFP using a 2A ribosomal skipping sequence. Cultures are re-stimulated with either CD19+ K562 cells (K562-CD19), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. GFP+ T cells are enumerated by flow cytometry using bead-based counting.

Sustained TFP+ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with alphaCD3/alphaCD28 coated magnetic beads on day 0, and transduction with the indicated TFP on day 1.

Animal models can also be used to measure a TFP-T activity. For example, xenograft model using human CD19-specific TFP+ T cells to treat a primary human pre-B ALL in immunodeficient mice can be used. Very briefly, after establishment of ALL, mice are randomized as to treatment groups. Different numbers of engineered T cells are coinjected at a 1:1 ratio into NOD-SCID-.gamma.−/− mice bearing B-ALL. The number of copies of each vector in spleen DNA from mice is evaluated at various times following T cell injection. Animals are assessed for leukemia at weekly intervals. Peripheral blood CD19+B-ALL blast cell counts are measured in mice that are injected with alphaCD19−.zeta. TFP+ T cells or mock-transduced T cells. Survival curves for the groups are compared using the log-rank test. In addition, absolute peripheral blood CD4+ and CD8+ T cell counts 4 weeks following T cell injection in NOD-SCID-.gamma.−/− mice can also be analyzed. Mice are injected with leukemic cells and 3 weeks later are injected with T cells engineered to express TFP by a bicistronic lentiviral vector that encodes the TFP linked to eGFP. T cells are normalized to 45-50% input GFP+ T cells by mixing with mock-transduced cells prior to injection, and confirmed by flow cytometry. Animals are assessed for leukemia at 1-week intervals. Survival curves for the TFP+ T cell groups are compared using the log-rank test.

Dose dependent TFP treatment response can be evaluated. For example, peripheral blood is obtained 35-70 days after establishing leukemia in mice injected on day 21 with TFP T cells, an equivalent number of mock-transduced T cells, or no T cells. Mice from each group are randomly bled for determination of peripheral blood CD19+ ALL blast counts and then killed on days 35 and 49. The remaining animals are evaluated on days 57 and 70.

Assessment of TFP-mediated proliferation is performed in microtiter plates by mixing washed T cells with K562 cells expressing CD19 (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T cell expansion ex vivo. T cells are enumerated in cultures using CountBright™ fluorescent beads (Invitrogen, Carlsbad, Calif.) and flow cytometry as described by the manufacturer. TFP+ T cells are identified by GFP expression using T cells that are engineered with eGFP-2A linked TFP-expressing lentiviral vectors. For TFP+ T cells not expressing GFP, the TFP+ T cells are detected with biotinylated recombinant CD19 protein and a secondary avidin-PE conjugate. CD4+ and CD8+ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by a standard 51Cr-release assay. Briefly, target cells (K562 lines and primary pro-B-ALL cells) are loaded with 51Cr (as NaCrO4, New England Nuclear, Boston, Mass.) at 37 C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37 C., supernatant from each well is harvested. Released 51Cr is then measured using a gamma particle counter (Packard Instrument Co., Waltham, Mass.). Each condition is performed in at least triplicate, and the percentage of lysis is calculated using the formula: % Lysis, (ER-SR)/(TR-SR), where ER represents the average 51Cr released for each experimental condition.

Imaging technologies can be used to evaluate specific trafficking and proliferation of TFPs in tumor-bearing animal models. NOD/SCID/.gamma.c −/− (NSG) mice may be injected IV with Nalm-6 cells followed 7 days later with T cells 4 hour after electroporation with the TFP constructs. The T cells are stably transfected with a lentiviral construct to express firefly luciferase, and mice are imaged for bioluminescence. Alternatively, therapeutic efficacy and specificity of a single injection of TFP+ T cells in Nalm-6 xenograft model can be measured as the following: NSG mice are injected with Nalm-6 transduced to stably express firefly luciferase, followed by a single tail-vein injection of T cells electroporated with CD19 TFP 7 days later. Animals are imaged at various time points post injection. For example, photon-density heat maps of firefly luciferase positive leukemia in representative mice at day 5 (2 days before treatment) and day 8 (24 hr post TFP+ PBLs) can be generated.

Other assays, including those described in the Example section herein as well as those that are known in the art can also be used to evaluate the Anti-CD19 TFP constructs of the present disclosure.

Additives

Any of the compositions of the present disclosure may further comprise an excipient. The term "excipient" includes any and all solvents, dispersion media, coatings, antibacterial and antifungal agents, isotonic and absorption delaying agents and the like. The use of such media and agents for active substances or biological compounds is well known in the art. Except insofar as any conventional media or agent is incompatible with the active ingredient, its use in the therapeutic compositions of the disclosure is contemplated.

The term "excipient" is intended to include vehicles and carriers capable of being co-administered with a compound or biologic to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with multi-binding compounds also falls within the scope of the present disclosure.

In making the compositions of this disclosure, the active ingredient (e.g., a construct comprising an antibody) can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the subject by employing procedures known in the art.

In some cases, the compositions described herein may comprise an excipient that can provide long term preservation, bulk up a formulation that contains potent active ingredients, facilitate absorption, reduce viscosity, add flavoring, or enhance the solubility of the pharmaceutical composition. Non-limiting examples of excipients can include anti-adherents, binders (e.g., sucrose, lactose, starches, cellulose, gelatin, or polyethylene glycol), coatings (e.g., hydroxypropyl methylcellulose or gelatin), disintegrants, dyes, flavors (e.g., mint, peach, raspberry, or vanilla), glidants, lubricants, preservatives (e.g., acids, esters, phenols, mercurial compounds, or ammonium compounds), sorbents, or vehicles (e.g., petroleum or mineral oil).

Sequencing

Sequencing may be performed in some embodiments of the present disclosure, sequencing may be used. For example, sequencing of genomic DNA or tumor-derived nucleic acids may be performed to determine a nucleic acid sequence corresponding to a CLSMP expressed by a cell of a subject. Sequencing a nucleic acid can be performed using any method known in the art. In some embodiments, sequencing can include next generation sequencing. In some embodiments, sequencing the nucleic acid can be performed using chain termination sequencing, hybridization sequencing, Illumina sequencing, ion torrent semiconductor sequencing, mass spectrophotometry sequencing, massively parallel signature sequencing (MPSS), Maxam-Gilbert sequencing, nanopore sequencing, polony sequencing, pyrosequencing, shotgun sequencing, single molecule real time (SMRT) sequencing, SOLiD sequencing, or any combination thereof.

The number or the average number of times that a particular nucleotide within the nucleic acid is read during the sequencing process (e.g., the sequencing depth) can be multiple times larger than the length of the nucleic acid being sequenced. In some instances, when the sequencing depth is sufficiently larger (e.g., by at least a factor of 5) than the length of the nucleic acid, the sequencing can be referred to as 'deep sequencing'. In any of the embodiments disclosed herein, analyzing the nucleic acid can comprise deep sequencing. For example, a nucleic acid can be sequenced such that the sequencing depth is about 20 times greater than the length of the nucleic acid. In some instances, when the sequencing depth is at least about 100 times greater than the length of the nucleic acid, the sequencing can be referred to as 'ultra-deep sequencing'. In any of the embodiments disclosed herein, analyzing the nucleic acid can comprise ultra-deep sequencing. In some embodiments, the sequencing depth can be one average at least about 5 times greater, at least about 10 times greater, at least about 20 times greater, at least about 30 times greater, at least about 40 times greater, at least about 50 times greater, at least about 60 times greater, at least about 70 times greater, at least about 80 times greater, at least about 90 times greater, at least about 100 times greater than the length of the nucleic acid being sequenced.

Exemplary Applications for Anti Idiotype Therapies

Treatment of B Cell Malignancy—

B cell malignancies include chronic lymphocytic leukemia (CLL), mantle cell lymphoma (MCL) and follicular lymphoma (FL). These diseases are characterized by an indolent but relentless course. CLL, MCL and FL are caused by the aberrant clonal proliferation of B lymphocyte or B lymphocyte progenitors. Cells of these cancers express a B cell receptor (BCR) with an idiotype that is unique to the tumor lineage. Tumor cells can readily be obtained through biopsy, or in the case of CLL a blood sample. The sequence of the idiotype, including assessment of microheterogeneity, can be assessed through selective sequence amplification followed by molecular sequence analysis. PCR cloned idiotype genes from a cancer can be used to develop anti idiotype therapies as described in the present disclosure, using methods as described in the present disclosure. In one example, the therapeutic can be administered intravenously. When administered, the therapeutic can induce immune cells to attack and kill the cancer cells. A similar mechanism is the basis for the widely used drug rituximab, but rituximab can also provoke immune reactions against a wide range of normal cells including all of the subject's B lymphocytes. As a result, rituximab has many serious side effects. The increased targeting selectivity (e.g., the ability to selectively target cancer cells) of the methods and compositions of the present disclosure provides a safer and less toxic alternative to current treatments.

Treatment of T Cell Malignancy—

T cell malignancies include several distinct varieties of T cell lymphoma. These diseases may be characterized by an aggressive course and are frequently refractory to currently available therapies. Cells of these cancers express a T cell receptor (TCR) with an idiotype that is unique to the tumor lineage. Tumor cells can readily be obtained through biopsy or a blood sample. The sequence of the idiotype, including assessment of microheterogeneity, can be assessed through selective sequence amplification followed by molecular sequence analysis. PCR cloned idiotype genes from a cancer can be used to develop an anti idiotype therapeutic as described in the present disclosure, using methods as described in the present disclosure. The therapeutic can be administered intravenously. When administered, the therapeutic can induce immune cells to attack and kill the cancer cells. A similar mechanism is the basis for the widely used drug rituximab, but rituximab can also provoke immune reactions against a wide range of normal cells including all of the subject's B lymphocytes. As a result, rituximab has many serious side effects. The increased targeting selectivity (e.g., the ability to selectively target cancer cells) of the methods and compositions of the present disclosure provides a safer and less toxic alternative to current treatments.

Treatment of Autoimmune Disease—

Autoimmune diseases including rheumatoid arthritis and Sjogren's syndrome are characterized by the presence of abnormal anti-self antibodies. In many subjects, these autoantibodies can be produced by a single abnormal clonal lineage of B lymphocytes. These abnormal B lymphocytes are enriched at sites of inflammation such as inflamed joints, and these cells can readily be obtained by joint aspiration. The B lymphocytes producing the abnormal antibody also express that antibody on their cell surface. The sequence of the idiotype, including assessment of microheterogeneity, can be assessed through selective sequence amplification followed by molecular sequence analysis. PCR cloned idiotype genes from a cancer can be used to develop an anti idiotype therapeutic as described in the present disclosure, using methods as described in the present disclosure. The therapeutic can be administered intravenously. When administered, the therapeutic will induce immune cells to attack and kill the clonal lineage of B lymphocytes producing the abnormal anti-self antibodies to prevent the development or progression of arthritis. A similar mechanism is the basis for the drug rituximab which is used in severe cases of rheumatoid arthritis where other treatments have failed. Rituximab also provokes immune reactions against a wide range of normal cells including all of the subject's B lymphocytes. As a result, rituximab has many serious side effects. The increased targeting selectivity (e.g., the ability to selectively target cancer cells) of the methods and compositions of the present disclosure provides a safer and less toxic alternative to current treatments.

Exemplary Applications for Anti Idiotype Targeting Therapies with Unmutated IGHV Genes Treatment of B Cell Malignancy—

B cell malignancies include chronic lymphocytic leukemia (CLL), mantle cell lymphoma (MCL) and follicular lymphoma (FL). These diseases are characterized by an indolent but relentless course. CLL, MCL and FL are caused by the aberrant clonal proliferation of B lymphocyte or B lymphocyte progenitors. Cells of these cancers express a B cell receptor (BCR) with an idiotype that is unique to the tumor lineage. In an aggressive subset of CLL and in most MCL cancers, the IGHV genes are rearranged, but do not undergo somatic cell hyper mutation. Tumor cells can readily be obtained through biopsy, or in the case of CLL a blood sample. The sequence of the idiotype, including assessment of microheterogeneity, can be assessed through selective sequence amplification followed by molecular sequence analysis. Sequence analysis will permit the diagnosis of cancers where the IGHV gene is not undergoing somatic hyper mutation, and will allow the IGHV class and subclass to be rapidly determined. The appropriate IGHV class targeting therapeutic can then be selected from a pre manufactured panel of IGHV class specific therapeutics. The therapeutic can be administered intravenously. When administered, the therapeutic will induce immune cells to attack and kill the cancer cells. The compositions and/or methods of the present disclosure can be safer and less toxic than rituximab as they can selectively target B cells bearing one class or subclass of IGHV genes while leaving the remainder of the B cell repertoire intact.

CD19 Associated Diseases and/or Disorders

In some aspects, the present disclosure provides methods for treating a disease associated with, at least in part, CD19 expression (e.g., chronic lymphocytic leukemia). For example, the TFP of the present disclosure is useful for treating subjects that have undergone treatment for a disease associated with elevated expression of CD19, wherein the subject that has undergone treatment for elevated levels of CD19 exhibits a disease associated with elevated levels of CD19.

In one aspect, the present disclosure pertains to a vector comprising Anti-CD19 TFP operably linked to promoter for expression in mammalian T cells. In one aspect, the present disclosure provides a recombinant T cell expressing the CD19 TFP for use in treating CD19-expressing tumors, wherein the recombinant T cell expressing the CD19 TFP is termed a CD19 TFP-T. In one aspect, the CD19 TFP-T of the present disclosure is capable of contacting a tumor cell with at least one CD19 TFP of the present disclosure expressed on its surface such that the TFP-T targets the tumor cell and growth of the tumor is inhibited.

In one aspect, the present disclosure pertains to a method of inhibiting growth of a CD19-expressing tumor cell, comprising contacting the tumor cell with a CD19 TFP T cell of the present disclosure such that the TFP-T is activated in response to the antigen and targets the cancer cell, wherein the growth of the tumor is inhibited.

In one aspect, the present disclosure pertains to a method of treating cancer in a subject. The method comprises administering to the subject a CD19 TFP T cell of the present disclosure such that the cancer is treated in the subject. An example of a cancer that is treatable by the CD19 TFP T cell of the present disclosure is a cancer associated with expression of CD19. In one aspect, the cancer associated with expression of CD19 is a hematological cancer. In one aspect, the hematological cancer is a leukemia or a lymphoma. In one aspect, a cancer associated with expression of CD19 includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 expression include, but not limited to, e.g., atypical and/or non-classical cancers, malignancies, precancerous conditions or proliferative diseases associated with expression of CD19.

In some embodiments, a cancer that can be treated with a CD19 TFP, e.g., described herein, is multiple myeloma. Multiple myeloma is a cancer of the blood, characterized by accumulation of a plasma cell clone in the bone marrow. Current therapies for multiple myeloma include, but are not limited to, treatment with lenalidomide, which is an analog of thalidomide. Lenalidomide has activities which include anti-tumor activity, angiogenesis inhibition, and immunomodulation. Generally, myeloma cells are thought to be negative for CD19 expression by flow cytometry. The present disclosure encompasses the recognition that a small percent of myeloma tumor cells express CD19, as demonstrated in Example 6. Thus, in some embodiments, a C19 TFP, e.g., as described herein, may be used to target myeloma cells. In some embodiments, CD19 TFP therapy can be used in combination with one or more additional therapies, e.g., lenalidomide treatment.

The present disclosure includes a type of cellular therapy where T cells are genetically modified to express a TFP and the TFP-expressing T cell is infused to a recipient in need thereof. The infused cell is able to kill tumor cells in the recipient. Unlike antibody therapies, TFP-expressing T cells are able to replicate in vivo resulting in long-term persistence that can lead to sustained tumor control. In various aspects, the T cells administered to the subject, or their progeny, persist in the subject for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the subject.

In some aspects, the present disclosure also includes a type of cellular therapy where T cells are modified, e.g., by in vitro transcribed RNA, to transiently express a TFP and the TFP-expressing T cell is infused to a recipient in need thereof. The infused cell is able to kill tumor cells in the recipient. Thus, in various aspects, the T cells administered to the subject, is present for less than one month, e.g., three weeks, two weeks, one week, after administration of the T cell to the subject.

Without wishing to be bound by any particular theory, the anti-tumor immunity response elicited by the TFP-expressing T cells may be an active or a passive immune response, or alternatively may be due to a direct vs indirect immune response. In one aspect, the TFP transduced T cells exhibit specific proinflammatory cytokine secretion and potent cytolytic activity in response to human cancer cells expressing the CD19 antigen, resist soluble CD19 inhibition, mediate bystander killing and mediate regression of an established human tumor. For example, antigen-less tumor cells within a heterogeneous field of CD19-expressing tumor may be susceptible to indirect destruction by CD19-redirected T cells that has previously reacted against adjacent antigen-positive cancer cells.

In one aspect, the human TFP-modified T cells of the present disclosure may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a TFP to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a TFP disclosed herein. The TFP-modified cell can be administered to a mammalian recipient to provide a therapeutic benefit. The mammalian recipient may be a human and the TFP-modified cell can be autologous with respect to the recipient. Alternatively, the cells can be allogeneic, syngeneic or xenogeneic with respect to the recipient.

Ex vivo expansion of hematopoietic stem and progenitor cells can be applied to the cells of the present disclosure. Other suitable methods are known in the art, therefore the present disclosure is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition, cellular growth factors such as flt3-L, IL-1, IL-3 and c-kit ligand, can be used for culturing and expansion of the cells.

In addition to using a cell-based vaccine in terms of ex vivo immunization, the present disclosure also provides compositions and methods for in vivo immunization to elicit an immune response directed against an antigen in a subject.

Generally, the cells activated and expanded as described herein may be utilized in the treatment and prevention of diseases that arise in subjects who are immunocompromised. In particular, the TFP-modified T cells of the present disclosure are used in the treatment of diseases, disorders and conditions associated with expression of CD19. In certain aspects, the cells of the present disclosure are used in the treatment of subjects at risk for developing diseases, disorders and conditions associated with expression of CD19. Thus, the present disclosure provides methods for the treatment or prevention of diseases, disorders and conditions associated with expression of CD19 comprising administering to a subject in need thereof, a therapeutically effective amount of the TFP-modified T cells of the present disclosure.

In one aspect the TFP-T cells of the present disclosure may be used to treat a proliferative disease such as a cancer or malignancy or is a precancerous condition such as a myelodysplasia, a myelodysplastic syndrome or a preleukemia. In one aspect, the cancer is a hematological cancer. In one aspect, the hematological cancer is a leukemia or a lymphoma. In one aspect, the TFP-T cells of the present disclosure may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 expression include, but not limited to, e.g., atypical and/or non-classical cancers, malignancies, precancerous conditions or proliferative diseases expressing CD19. Non-cancer related indications associated with expression of CD19 include, but are not limited to, e.g., autoimmune disease, (e.g., lupus), inflammatory disorders (allergy and asthma) and transplantation.

The TFP-modified T cells of the present disclosure may be administered either alone, or as a pharmaceutical composition in combination with diluents and/or with other components such as IL-2 or other cytokines or cell populations.

Hematologic Cancer

Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

The present disclosure provides for compositions and methods for treating cancer. In one aspect, the cancer is a hematologic cancer including but is not limited to hematological cancer is a leukemia or a lymphoma. In one aspect, the TFP-T cells of the present disclosure may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 expression includes, but not limited to, e.g., atypical and/or non-classical cancers, malignancies, precancerous conditions or proliferative diseases expressing CD19.

The present disclosure also provides methods for inhibiting the proliferation or reducing a CD19-expressing cell population, the methods comprising contacting a population of cells comprising a CD19-expressing cell with an anti-CD19 TFP-T cell of the present disclosure that binds to the CD19-expressing cell. In a specific aspect, the present disclosure provides methods for inhibiting the proliferation or reducing the population of cancer cells expressing CD19, the methods comprising contacting the CD19-expressing cancer cell population with an anti-CD19 TFP-T cell of the present disclosure that binds to the CD19-expressing cell. In one aspect, the present disclosure provides methods for inhibiting the proliferation or reducing the population of cancer cells expressing CD19, the methods comprising contacting the CD19-expressing cancer cell population with an anti-CD19 TFP-T cell of the present disclosure that binds to the CD19-expressing cell. In certain aspects, the anti-CD19 TFP-T cell of the present disclosure reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with CD19-expressing cells relative to a negative control. In one aspect, the subject is a human.

The present disclosure also provides methods for preventing, treating and/or managing a disease associated with CD19-expressing cells (e.g., a hematologic cancer or atypical cancer expressing CD19), the methods comprising administering to a subject in need an anti-CD19 TFP-T cell of the present disclosure that binds to the CD19-expressing cell. In one aspect, the subject is a human. Non-limiting examples of disorders associated with CD19-expressing cells include autoimmune disorders (such as lupus), inflammatory disorders (such as allergies and asthma) and cancers (such as hematological cancers or atypical cancers expressing CD19).

The present disclosure also provides methods for preventing, treating and/or managing a disease associated with CD19-expressing cells, the methods comprising administering to a subject in need an anti-CD19 TFP-T cell of the present disclosure that binds to the CD19-expressing cell. In one aspect, the subject is a human.

The present disclosure provides methods for preventing relapse of cancer associated with CD19-expressing cells, the methods comprising administering to a subject in need thereof an anti-CD19 TFP-T cell of the present disclosure that binds to the CD19-expressing cell. In one aspect, the methods comprise administering to the subject in need thereof an effective amount of an anti-CD19 TFP-T cell described herein that binds to the CD19-expressing cell in combination with an effective amount of another therapy.

Combination Therapies

A TFP-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the "at least one additional therapeutic agent" includes a TFP-expressing cell. Also provided are T cells that express multiple TFPs, which bind to the same or different target antigens, or same or different epitopes on the same target antigen. Also provided are populations of T cells in which a first subset of T cells express a first TFP, and a second subset of T cells express a second TFP.

A TFP-expressing cell described herein and the at least one additional therapeutic agent can be administered simultaneously, in the same or in separate compositions, or sequentially. For sequential administration, the TFP-expressing cell described herein can be administered first, and the additional agent can be administered second, or the order of administration can be reversed.

In further aspects, a TFP-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, irradiation, and peptide vaccine.

In one embodiment, the subject can be administered an agent which reduces or ameliorates a side effect associated with the administration of a TFP-expressing cell. Side effects associated with the administration of a TFP-expressing cell include, but are not limited to cytokine release syndrome (CRS), and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a TFP-expressing cell described herein to a subject and further administering an agent to manage elevated levels of a soluble factor resulting from treatment with a TFP-expressing cell. In one embodiment, the soluble factor elevated in the subject is one or more of IFN-.gamma., TNF-alpha, IL-2 and IL-6. Therefore, an agent administered to treat this side effect can be an agent that neutralizes one or more of these soluble factors. Such agents include, but are not limited to a steroid, an inhibitor of TNFalpha, and an inhibitor of IL-6. An example of a TNF-alpha inhibitor is entanercept. An example of an IL-6 inhibitor is tocilizumab (toc).

In one embodiment, the subject can be administered an agent which enhances the activity of a TFP-expressing cell. For example, in one embodiment, the agent can be an agent which inhibits an inhibitory molecule. Inhibitory molecules, e.g., Programmed Death 1 (PD1), can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a TFP-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the TFP-expressing cell. In an embodiment the inhibitor is an shRNA. In an embodiment, the inhibitory molecule is inhibited within a TFP-expressing cell. In these embodiments, a dsRNA molecule that inhibits expression of the inhibitory molecule is linked to the nucleic acid that encodes a component, e.g., all of the components, of the TFP. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

In some embodiments, the agent which enhances the activity of a TFP-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the TFP. In another embodiment, the fusion protein is expressed by a cell, e.g., a T cell that does not express an anti-CD19 TFP.

Other Embodiments

The section headings used herein are for organizational purposes only and are not to be construed as limiting the subject matter described.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims. While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the rage is present as if explicitly written out. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed.

EXAMPLES

Example 1. Treatment of Cancer in a Subject with Un-Mutated Chronic Lymphocytic Leukemia (CLL)

A subject presents with multiple symptoms, including fever, fatigue, and enlarged lymph nodes. A clinician non-invasively obtains a blood sample to perform a peripheral blood smear and flow cytometry, ultimately diagnosing the subject with chronic lymphocytic leukemia (CLL). A portion of the blood sample is fractionated to isolate the buffy coat, and deep sequencing of genomic DNA from the CLL leukemia B-cells is performed, thereby determining that the IGHV1-69 allele exhibits greater than 98% sequence homology to the germline IGHV gene. Prognosticating an aggressive disease course, the clinician prescribes a personalized therapy using an antibody that binds to an Fc receptor on an effector cell and the specific gene product of the IGHV1-69 allele sequenced from the subject's CLL B-cells. The subject is pre-medicated with diphenhydramine (50 mg) and acetaminophen (500 mg to 1000 mg) 30 minutes prior to first antibody infusion. Three days per week, on alternating days, over a period of 12 weeks, the subject is intravenously administered 30 milligrams of antibody by slow infusion over a period of 2 hours. The subject is routinely monitored for infections during, and for a period of 2 months following, treatment. After several months of treatment, a blood sample is obtained, and a peripheral blood smear and flow cytometry show no indication of CLL.

Example 2. Treatment of an Autoimmune Disease in a Subject

A subject is diagnosed with rheumatoid arthritis, a disease characterized by the presence of abnormal anti-self antibodies produced by a single abnormal clonal lineage of B lymphocytes that express the antibodies on their cell surface. A biopsy of the diseased B lymphocytes is obtained, and the sequence of the idiotype, including assessment of microheterogeneity, is determined through selective sequence amplification followed by molecular sequence analysis. The amplicons encoding the idiotype genes are used to develop an anti idiotype therapeutic antibody having one domain with an affinity for the abnormal anti-self antibody produced by diseased B lymphocytes, and a second domain with an affinity for an Fc receptor (e.g., such as those found on effector cells). When administered the subject, the therapeutic antibody induces immune cells to attack and kill the clonal lineage of B lymphocytes producing the abnormal anti-self antibodies, thereby preventing the development or progression of arthritis. The increased targeting selectivity (e.g., the ability to selectively target cancer cells) of the methods and compositions of the present disclosure provides a safer and less toxic alternative to current treatments (e.g., Rituximab).

Example 3. Monoclonal Antibody Production Using Hybridoma Technology

Hybridomas can be used to make the constructs (e.g., antibodies) of the present disclosure, and are generated by immunizing mice with live patient derived tumor cells or membrane extracts made therefrom. The mice are inoculated intraperitoneally with an immunogenic amount of the cells or extract and then boosted with similar amounts of the immunogen. Spleens are collected from the immunized mice, and hybridomas are prepared from the splenocytes and a murine tumor partner using a somatic cell hybridization technique. Tumor cells and splenocytes are fused using the fusogen polyethylene glycol. The fused cells are separated from the fusion medium and grown in a HAT selective growth medium to eliminate unhybridized parent cells. The hybridomas are expanded, and supernatants are assayed for anti-tumor activity by solid-phase enzyme-linked immunosorbent assay (ELISA) using the immunizing agent (tumor cells or membrane extracts made therefrom) as an antigen. Briefly, 40 µl of 0.1 mg/ml tumor-derived cell membrane protein are placed in polyvinyl chloride (PVC) microtiter wells for 12 hr at 4° C. The extract is aspirated and the wells washed with phosphate buffered saline (PBS) containing 1% bovine serum albumin (BSA). The wells are subsequently incubated with 45 µl of a 1:10 dilution of hybridoma supernatant. The diluent is a media with 25 mM of a buffer, 10% bovine serum, and 0.1% sodium azide. After 30 min at room temperature, the wells are washed and subsequently incubated for 45 min at 37° C. with a 1:200 dilution of peroxidase conjugated goat anti-mouse IgG. Following incubation, the wells are washed with PBS and reacted with 200 µl of 2,2-azino-di(3-ethylbenzthiazoline sulphonic acid) in 0.1M sodium citrate buffer pH 4.2 for 30 min at room temperature. Hybridomas corresponding to wells that exhibit a reaction on the tumor-derived cell membrane extract of greater than 0.7 O.D. are grown in vitro. Monoclonal antibodies are isolated from the culture media of these hybridomas using ammonium sulfate precipitation, chromatography, and/or ultrafiltration.

What is claimed is:
1. A method of preparing an idiotype-specific monoclonal antibody or fragment thereof, the method comprising:
   a) obtaining a biological sample from a subject having a leukemia or lymphoma, the biological sample comprising malignant lymphocytes;
   b) enriching the biological sample for a plurality of lymphocytes comprising a clonal lineage specific marker protein (CLSMP) derived from a gene, wherein the gene is selected from the group consisting of IGHV1-69, IGHV1-2, IGHV4-39, IGHV3-30, IGHV4-34, IGHV3-11, IGHV3-48, IGHV1-3, IGHV3-21, IGHV3-23, IGHV1-18, IGHV1-46, IGHV3-33, IGHV3-7, IGHV3-9, IGHV4-59, IGHV1-24, IGHV2-5, IGHV2-70, IGHV3-15, IGHV3-30-3, IGHV3-74, IGHV5-10-1, IGHV5-51, IGHV3-48, IGHV1-45, IGHV1-8, IGHV2-26, IGHV3-20, IGHV3-49, IGHV3-53, IGHV3-72, IGHV3-73, IGHV4-31, IGHV4-38-2, and IGHV7-4, and wherein the CLSMP comprises a B cell receptor (BCR) idiotype;
   c) performing reverse transcription on a plurality of RNA molecules corresponding to the CLSMP expressed in the enriched plurality of lymphocytes, thereby generating a plurality of cDNA molecules;

d) amplifying the plurality of cDNA molecules, thereby generating a plurality of individually-separated PCR amplicons;

e) performing massively parallel sequencing of the plurality of amplicons, thereby generating a plurality of sequence reads;

f) clustering the plurality of sequence reads by similarity to generate a set of cluster-representative sequences;

g) rank ordering the set of cluster-representative sequences by abundance identify a clonally-specific idiotype gene based on abundant expression in the plurality of lymphocytes;

h) expressing an idiotype protein corresponding to the clonally-specific idiotype gene; and i) selecting an idiotype-specific monoclonal antibody or fragment thereof that binds the clonally-specific idiotype, wherein the idiotype-specific monoclonal antibody or fragment thereof is selected from a phagemid display library comprising phage expressing a plurality of antibodies, Fab domains or scFv domains.

2. The method of claim 1, wherein the subject has leukemia or lymphoma selected from the group consisting of chronic lymphocytic leukemia (CLL), acute lymphocytic leukemia (ALL), acute myeloid leukemia (AML), mantle cell lymphoma (MCL), diffuse large B cell lymphoma (DLBCL), and follicular lymphoma (FL).

3. The method of claim 1, further comprising aligning the set of cluster-representative sequences to a reference that corresponds to a sequence analysis generated by sequencing a second plurality of nucleic acid molecules prepared from a reference biological sample from the subject, wherein the reference biological sample comprises a second plurality of cells, and wherein the reference biological sample is not enriched for a plurality of cells comprising the CLSMP.

4. The method of claim 1, wherein the idiotype-specific monoclonal antibody or fragment thereof comprises a single chain variable fragment (scFv) domain.

5. The method of claim 1, wherein the CLSMP is derived from the IGHV1-69 gene.

6. The method of claim 1, wherein the BCR idiotype comprises an IGHV gene product associated with at least one of an IGLV gene product or an IGKV gene product.

7. The method of claim 1, wherein the leukemia or lymphoma is chronic lymphocytic leukemia (CLL) and the CLSMP is derived from IGHV1-69.

8. The method of claim 1, wherein the idiotype-specific monoclonal antibody is a bispecific antibody.

9. The method of claim 1, wherein the idiotype-specific fragment is a fragment of a bi-specific T-cell engager.

* * * * *

UNITED STATES PATENT AND TRADEMARK OFFICE
CERTIFICATE OF CORRECTION

PATENT NO. : 10,221,249 B2
APPLICATION NO. : 15/261084
DATED : March 5, 2019
INVENTOR(S) : David J. States et al.

Page 1 of 1

It is certified that error appears in the above-identified patent and that said Letters Patent is hereby corrected as shown below:

In the Claims

At Column 69, Line number 12, Claim 1 insert the word -- to -- after the word "abundance" and before the word "identify".

Signed and Sealed this
Twenty-first Day of May, 2019

Andrei Iancu
*Director of the United States Patent and Trademark Office*